US006939955B2

(12) United States Patent
Rameshwar

(10) Patent No.: US 6,939,955 B2
(45) Date of Patent: Sep. 6, 2005

(54) HEMATOPOIETIC GROWTH FACTOR INDUCIBLE NEUROKININ-1 GENE

(75) Inventor: Pranela Rameshwar, Maplewood, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 556 days.

(21) Appl. No.: 10/039,272

(22) Filed: Oct. 20, 2001

(65) Prior Publication Data

US 2002/0168653 A1 Nov. 14, 2002

Related U.S. Application Data

(60) Provisional application No. 60/241,881, filed on Oct. 20, 2000.

(51) Int. Cl.$^7$ .......................... C07H 21/02; C07H 21/04
(52) U.S. Cl. .................... 536/23.5; 536/23.1; 536/23.2; 435/6
(58) Field of Search .................. 435/6, 320.1, 325, 435/69.1; 536/23.5

(56) References Cited

PUBLICATIONS

Rubanyi (Mol. Aspects Med. (2001) 22:113–142).*
Verma et al. (1997) Nature vol. 389, p. 239–242.*
Marshall (1995) Science, vol. 269, Issue 5227, pp. 1050–1055.*
Eck et al. (Goodman & Gilman's The Pharmacological Basis of Therapeutics (1996), 9th Edition, Chapter 5, McGraw–Hill, NY).*
Juengst (British Medical Journal (2003) vol. 326, pp. 1410–1411).*
Abrahams et al., "Cyclic AMP regulates the expression of neurokinin$_1$ receptors by neonatal rat spinal neurons in culture," J. Neurochem., vol. 73, No. 1, (1999) pp. 50–58.
Adamus et al., Effect of the neuropeptide substance P on the rat bone marrow–derived osteogenic cells in vitro, J. Cell. Biochem., vol. 81, (2001) pp. 499–506.
Bairoch et al., "The PROSITE database, its status in 1997," Nucleic Acid Res., vol. 25, No. 1, (1997) pp. 217–221.
Biggs et al., "A human Id–like helix–loop–helix protein expression during early development," Proc. Nat'l Acad. Sci. USA, vol. 89, (1992) pp. 1512–1516.
Cooper et al., "Differential expression of Id genes in multipotent myeloid progenitor cells: Id–1 is induced by early– and late–acting cytokines while Id–2 is selectively induced by cytokines that drive terminal granulocytic differentiation," J. Cell. Biochem., vol. 71, (1998) pp. 277–285.
Corpet et al., "The ProDom database of protein domain families," Nucleic Acid Res., vol. 26, No. 1, (1998) pp. 323–326.
Gerard et al., "Human substance P receptor (NK–1): organization of the gene, chromosome localization, and functional expression of cDNA clones," Biochemistry, vol. 30, (1991) pp. 10640–10646.
Hegde et al., "c–Maf induces monocytic differentiation and apoptosis in bipotent myeloid progenitors," Blood, vol. 94, No. 5, (Sep. 1, 1999) pp. 1578–1589.
Ho et al., "Human monocytes and macrophages express substance P and neurokinin–1 receptor," J Immunol., vol. 159, (1997) pp. 5654–5660.
International Polycystic Kidney Disease Consortium, The, "Polycystic kidney disease: The complete structure of the PKD1 gene and its protein," Cell, vol. 81, (1995) pp. 289–298.
Ishiguro et al., "Id2 expression increases with differentiation of human myeloid cells," Blood, vol. 87, No. 12, (1996) pp. 5225–5231.
Krause et al., "Structure, functions, and mechanisms of substance P receptor action," J. Invest. Dermatol., vol. 98, No. 6, (Jun. 1992) pp. 2S–7S.
Maggi, "Tachykinins in the autonomic nervous system," Pharmacol. Res., vol. 33, No. 3, (1996) pp. 161–170.
Marriott et al., "IL–4 and IFN–γ up–regulate substance P receptor expression in murine peritoneal macrophages," J. Immunol., vol. 165, No. 1, (2000) pp. 182–191.
Massari et al., "Helix–Loop–Helix proteins: Regulators of transcription in eucaryotic organisms," Mol. Cell. Biol., vol. 20, No. 2, (Jan. 2000) pp. 429–440.
Miura et al., "Pyk2 and Syk participate in functional activation of granulocytic HL–60 cells in a different manner," Blood, vol. 96, No. 5,(Sep. 1, 2000) pp. 1733–1739.
Muller–Sieburg et al., "The stromal cells' guide to the stem cell universe," Stem Cells, vol. 13, (1995) pp. 477–486.
Norton et al., "Id helix–loop–helix proteins in cell growth and differentiation," Trends Cell Biol., vol. 8, (Feb. 1998) pp. 58–65.

(Continued)

Primary Examiner—Jeffrey Siew
Assistant Examiner—Brandon Fetterolf
(74) Attorney, Agent, or Firm—Licata & Tyrrell P.C.

(57) ABSTRACT

Bone marrow (BM) is the major organ where immune cells are derived. Homeostasis in the BM is maintained by inter- and intra-cellular interactions by the various subsets of BM cells. The present invention discloses the cloning of a new cDNA from stimulated BM stromal cells that was retrieved with a probe specific for the neurokinin-1 (NK-1) receptor. The cloned cDNA was designated 'Hematopoietic Growth Factor Inducible Neurokinin-1 type' (HGFIN) gene based on its expression in differentiated hematopoietic cells. Hence, the present invention provides a novel gene, HGFIN, which encodes a protein receptor that is involved in the regulation of hematopoietic proliferation and differentiation. The protein of the present invention may be involved as a central mediator of white blood cell, progenitor, differentiation, and therefore, may be useful in the prevention and treatment of lymphoproliferative syndromes such as B-cell related maladies, including but not limited to acute and chronic myeloid and lymphocytic leukemia as well as the B-cell subtype of Hodgkin's and non-Hodgkin's lymphomas.

8 Claims, 10 Drawing Sheets

OTHER PUBLICATIONS

Quinn et al., "Molecular models to analyse preprotachykinin–A expression and function," Neuropeptides, vol. 34, No. 5, (2000) pp. 292–302.

Rameshwar, "Substance P: A regulatory neuropeptide for hematopoiesis and immune functions," Clin. Immunol. Immunopath., vol. 85, No. 2, (2000) pp. 129–133.

Rameshwar et al., "Hematopoietic regulation mediated by interactions among the neurokinins and cytokines," Leuk. Lymphoma, vol. 28, (1997) pp. 1–10.

Rameshwar et al., "Receptor induction regulates the synergistic effects of substance P with IL–1 and PDGF on the proliferation of bone marrow fibroblasts," J. Immunol., vol. 158, (1997) pp. 3417–3424.

Rameshwar et al., "Mimicry between neurokinin–1 and fibronectin may explain the transport and stability of increased substance P–immunoreactivity in patients with bone marrow fibrosis," Blood, vol. 97, No. 10, (May 15, 2001) pp. 3025–3031.

Rameshwar et al., "NF–κB as a central mediator in the induction of TGF–β in monocytes from patients with idiopathic myelofibrosis: An inflammatory response beyond the realm of homeostasis," J. Immunol., vol. 165, (2000) pp. 2271–2277.

Randall, "Characterization of a population of cells in the bone marrow that phenotypically mimics hematopoietic stem cells: resting stem cells or mystery population?" Stem Cells, vol. 16, (1998) pp. 38–48.

Roodman, "Cell biology of the osteoclast," Exp. Hematol., vol. 27, (1999) pp. 1229–1241.

Rost et al., "Combining evolutionary information and neural networks to predict protein secondary structure," Proteins, vol. 19, (1994) pp. 55–72.

Rost et al., "Prediction of protein structure at better than 70% accuracy," J. Mol. Biol., vol. 232, (1993) pp. 584–599.

Rupniak, "Discovery of the anti–depressant and anti–emetic efficacy of substance P receptor ($NK_1$) antagonists," Tachykinins 2000, p. 2a.

Singh et al., "Increased expression of preprotachykinin–1 and neurokinin receptors in human breast cancer cells. Implications for bone marrow metastasis," Proc. Nat'l Acad. Sci. USA, vol. 97, No. 1, (Jan. 4, 2000) pp. 388–393.

Sonnhammer, E.L., G. Heijne, and A. Krogh. 1998. A hidden Markov model for predicting transmembrane helices in protein sequences. pp. 175–182. In Ed J. Glasgow, T. Littlejohn, F. Major, R. Lathrop, D. Sankoff, and C. Sensen (ed.), Proceedings of $6^{th}$ International Conference on Intelligent Systems for Molecular Biology. Menlo Park, CA.

Tabarowski et al., "Noradrenergic and peptidergic innervation of the mouse femur bone marrow," Acta. Histochem., vol. 98, (1996) pp. 453–457.

Weterman et al., "nmb, a novel gene, is expressed in low–metastatic human melanoma cell lines and xenografts," Int. J. Cancer, vol. 60, (1995) pp. 73–81.

Yao et al., "Neurokinin–1 expression and colocalization with glutamate and GABA in the hypothalamus of the cat," Mol. Brain Res., vol. 71, (1999) pp. 149–158.

* cited by examiner

| | | | | | |
|---|---|---|---|---|---|
| 1 cggcacgagg | gcccagagga | auaaguuaac | cuuggugccu | gcguccguga | gaauucagca |

| 61 uggaaugucu | cuacuauuuc | cugggauuuc | ugcuccuggc | ugcaagauug | ccacuugaug |
|---|---|---|---|---|---|
| M E C L | Y Y F | L G F | L L L A | A R L | P L D |
| 121 ccgccaaacg | auuucaugau | gugcugggca | augaaagacc | uucugcuuac | augagggagc |
| A A K R | F H D | V L G | N E R P | S A Y | M R E |
| 181 acaaucaauu | aaauggcugg | ucuucugaug | aaaaugacug | gaaugaaaaa | cucuacccag |
| H N Q L | N G W | S S D | E N D W | N E K | L Y P |
| 241 uguggaagcg | gggagacaug | aggugaaaaa | acuccuggaa | gggaggccgu | gugcaggcgg |
| V W K R | G D M | R W K | N S W K | G G R | V Q A |
| 301 uccugaccag | ugacucacca | gcccucgugg | gcucaaauau | aacauuugcg | gugaaccuga |
| V L T S | D S P | A L V | G S N I | T F A | V N L |
| 361 uauucccuag | augccaaaag | gaagaugcca | auggcaacau | agucuaugag | aagaacugca |
| I F P R | C Q K | E D A | N G N I | V Y E | K N C |
| 421 gaaaugaggc | ugguuuaucu | gcugauccau | auguuuacaa | cuggacagca | uggucagagg |
| R N E A | G L S | A D P | Y V Y N | W T A | W S E |
| 481 acagugacgg | ggaaaauggc | accggccaaa | gccaucauaa | cgucuuccu | gaugggaaac |
| D S D G | E N G | T G Q | S H H N | V F P | D G K |
| 541 cuuuuccuca | ccaccccgga | uggagaagau | ggaauuucau | cuacgucuuc | cacacacuug |
| P F P H | H P G | W R R | W N F I | Y V F | H T L |
| 601 gucaguauuu | ccagaaauug | ggacgauguu | cagugagagu | uucugugaac | acagccaaug |
| G Q Y F | Q K L | G R C | S V R V | S V N | T A N |
| 661 ugacacuugg | gccucaacuc | auggaaguga | cugucuacag | aagacaugga | cgggcauaug |
| V T L G | P Q L | M E V | T V Y R | R H G | R A Y |
| 721 uucccaucgc | acaagugaaa | gauguguacg | ugguaacaga | ucagauuccu | guguuuguga |
| V P I A | Q V K | D V Y | V V T D | Q I P | V F V |
| 781 cuauguucca | gaagaacgau | cgaaauucau | ccgacgaaac | cuuccucaaa | gaucucccca |
| T M F Q | K N D | R N S | S D E T | F L K | D L P |
| 841 uuauguuuga | ugccugauu | caugauccua | gccacuuccu | caauuauucu | accauuaacu |
| I M F D | V L I | H D P | S H F L | N Y S | T I N |
| 901 acaaguggag | cuucggggau | aauacuggcc | uguuuguuuc | caccaaucau | acugugaauc |
| Y K W S | F G D | N T G | L F V S | T N H | T V N |
| 961 acacguaugu | gcucaaugga | accuucagcc | uuaaccucac | ugugaaagcu | gcagcaccag |
| H T Y V | L N G | T F S | L N L T | V K A | A A P |
| 1021 gaccuugucc | gccaccgcca | ccaccaccca | gaccuucaaa | acccaccccu | ucuuuaggac |
| G P C P | P P P | P P P | R P S K | P T P | S L G |
| 1081 cugcugguga | caaccccccug | gagcugagua | ggauuccuga | ugaaacugc | cagauuaaca |
| P A G D | N P L | E L S | R I P D | E N C | Q I N |
| 1141 gauauggcca | cuuucaagcc | accaucacaa | uuguagaggg | aaucuuagag | guuaacauca |
| R Y G H | F Q A | T I T | I V E G | I L E | V N I |

Fig.1A

```
1201 uccagaugac agacguccug augccgguge caugoccuga aagcucccua auagacuuug
      I  Q  M  T   D  V  L   M  P  V   P  W  P  E   S  S  L   I  D  F
1261 ucguqaccug ccaagggagc auucccacgg aggucuguac caucauuucu gaccccaccu
      V  V  T  C   Q  G  S   I  P  T   E  V  C  T   I  I  S   D  P  T
1321 gcgagaucac ccagaacaca gucugcagcc cuguggaugu ggaugagaug ugucugcuga
      C  E  I  T   Q  N  T   V  C  S   P  V  D  V   D  E  M   C  L  L
1381 cugugagacg aaccuucaau gggucuggga cguacugugu gaaccucacc cuggggaug
      T  V  R  R   T  F  N   G  S  G   T  Y  C  V   N  L  T   L  G  D
1441 acacaagccu ggcucucacg agcacccuga uuucuguucc ugacagagac ccagccucgc
      D  T  S  L   A  L  T   S  T  L   I  S  V  P   D  R  D   P  A  S
1501 cuuuaaggau ggcaaacagu gcccugaucu ccguuggcug cuuggccaua uugucacug
      P  L  R  M   A  N  S   A  L  I   S  V  G  C   L  A  I   F  T  V
1561 ugaucucccu cuugguguac aaaaaacaca aggaauacaa cccaauagaa aauaguccug
      I  S  L  L   V  Y  K   K  H  K   E  Y  N  P   I  E  N   S  P  G
1621 ggaauguggu cagaagcaaa ggccugagug ucuuucucaa ccgugcaaaa gccguuucu
      N  V  V  R   S  K  G   L  S  V   F  L  N  R   A  K  A   V  F  F
1681 ucccgggaaa ccaggaaaag gauccgcuac ucaaaaacca agaauuuaaa ggaguuucuu
      P  G  N  Q   E  K  D   P  L  L   K  N  Q  E   F  K  G   V  S
1741 aaauuucgac cuuguuucug aagcucacuu uucagugcca uugaugugag augugcugga
1801 guggcuauua accuuuuuuu ccuaaagauu auuguuaaau agauauugug guuuggggaa
1861 guugaauuuu uuauagguua aaugucauuu uagagauggg gagagggauu auacugcagg
1921 cagcuucagc caugungugu aacugauaaa agcaacuuag caaggcuucu uuucauuauu
1981 uuuuauguuu cacuuauaaa gucuuaggua acuaguagga uagaaacacu gugucccgag
2041 aguaaggaga gaagcuacua uugauuagag ccuaacccag guuaacugca agaagaggcg
2101 ggauacuuuc agcuuuccau guaacuguau gcauaaagcc aauguagucc aguuucuaag
2161 aucauguucc aagcuaacug aaucccacuu caauacacac ucaugaacuc cugauggaac
2221 aauaacaggc ccaagccugu gguaugaugu gcacacuugc uagacucaga aaaaauacua
2281 cucucauaaa ugggugggag uauuuuggug acaaccuacu uugcuuggcu gagugaagga
2341 augauauuca uauauucauu uauuccaugg acauuuaguu agugcuuuuu auauaccagg
2401 caugaugcug agugacacuc uuguguauau uuccaaauuu uuguauaguc gcugcacaua
2461 uuugaaauca aaauauuaag acuuuccaaa aauuuggucc cugguuuuuc auggcaacuu
2521 gaucaguaag gauuuccccu cuguuuggaa cuaaaaccau uuacuauaug uuagacaaga
2581 cauuuuuuuu uuuuccuucc ugaaaaaaaa augaggggaag agacaaaaaa aaaaaaaaaa
2641 aaaaaaaaaa aaaaaaaaaa aa
```

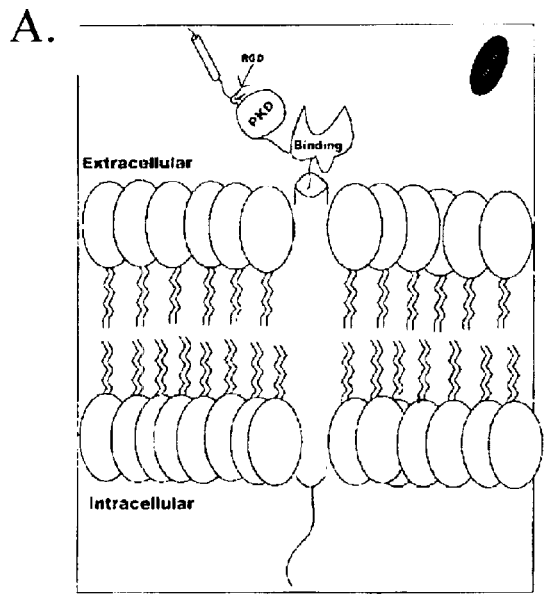

B.

```
  1 MECLYYFLGF LLLAARLPLD AAKRFHDVLG NERPSAYMRE HNQLNGWSSD
 51 ENDWNEKLYP VWKRGDMRWK NSWKGGRVQA VLTSDSPALV GSNITFAVNL
101 IFPRCQKEDA NGNIVYEKNC RNEAGLSADP YVYNWTAWSE DSDGENGTGQ
151 SHHNVFPDGK PFPHHPGWRR WNFIYVFHTL GQYFQKLGRC SVRVSVNTAN
201 VTLGPQLMEV TVYRRHGRAY VPIAQVKDVY VVTDQIPVFV TMFQKNDRNS
251 SDETFLKDLP IMFDVLIHDP SHFLNYSTIN YKWSFGDNTG LFVSTNHTVN
301 HTYVLNGTFS LNLTVKAAAP GPCPPPPPPP RPSKPTPSLG PAGDNPLELS
351 RIPDENCQIN RYGHFQATIT IVEGILEVNI IQMTDVLMPV PWPESSLIDF
401 VVTCQGSIPT EVCTIISDPT CEITQNTVCS PVDVDEMCLL TVRRTFNGSG
451 TYCVNLTLGD DTSLALTSTL ISVPDRDPAS PLRMANSALI SVGCLAIFVT
501 VISLLVYKKH KEYNPIENSP GNVVRSKGLS VFLNRAKAVF FPGNQEKDPL
551 LKNQEFKGVS
```

RGD = Cell Adhesion region
N = ASN Glycosylation Site
*PKD Region;*
Transmembrane

Fig.2

A. BMNC
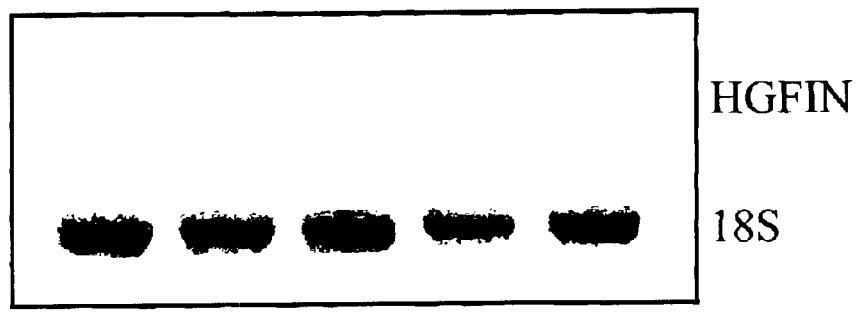
B. PBMC
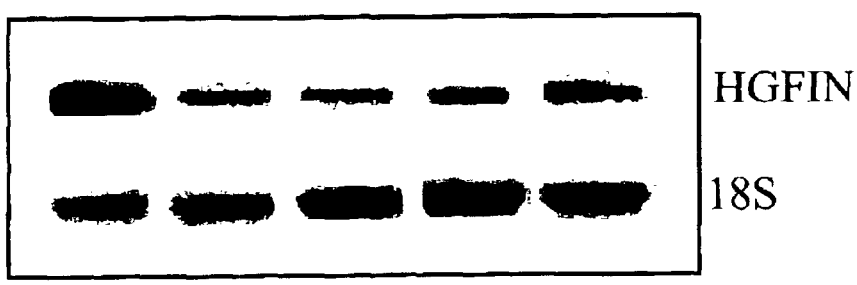
C. Differentiated BMNC
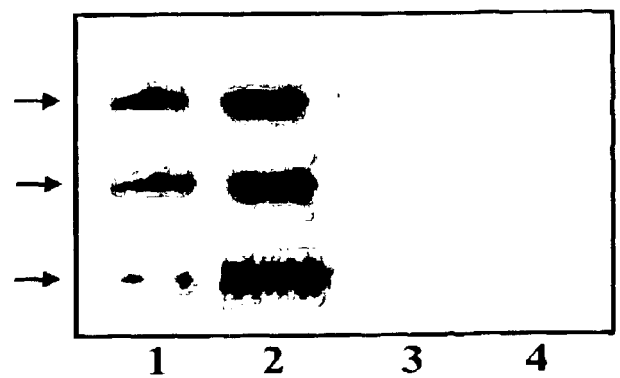
Fig.5

HEMATOPOIETIC GROWTH FACTOR INDUCIBLE NEUROKININ-1 GENE

The present utility patent application claims priority to provisional patent application U.S. Ser. No. 60/241,881 (Rameshwar et al.), filed Oct. 20, 2000, the disclosure of which is incorporated by reference in its entirety herein.

GOVERNMENT INTEREST

This invention was made with government support by the following Public Health Service grants: HL-54973 and HL-57675 from the National Institute of Health and CA89868 from the National Cancer Institute. The government may own certain rights in the present invention.

FIELD OF THE INVENTION

The present invention relates to the field of molecular biology, immunology, and the regulation of lymphocytic cell proliferation and differentiation. In particular, this invention provides a novel gene, Hematopoietic Growth Factor Inducible Neurokinin-1 Gene (HGFIN-1), which was isolated from stimulated human Bone Marrow stromal cells. HGFIN-1 plays an important role in inducing white blood cell differentiation and may play a role in inhibiting progenitor proliferation.

BACKGROUND OF THE INVENTION

Various publications or patents are referred to in parentheses throughout this application to describe the state of the art to which the invention pertains. Each of these publications or patents is incorporated by reference herein. Complete citations of scientific publications are set forth in the text or at the end of the specification.

Bone Marrow (BM) is the major source of both lymphocytes (immune cells) and erythrocytes in the adult. Among the various cells that constitute the BM are primitive hematopoietic pluripotent stem cells and progenitor cells. An important property of stem cells is their ability to both proliferate, which ensures a continuous supply throughout the lifetime of an individual, and differentiate into the mature cells of the peripheral blood system. When necessary, a pluripotent stem cell can begin to differentiate, and after successive divisions become committed, thus losing the capacity for self-renewal, to a particular line of development. All of the circulating blood cells, including erythrocytes, leukocytes or lymphocytes, granulocytes and platelets originate from various progenitor cells that are themselves derived from precursor stem cells.

The morphologically recognizable and functionally capable cells circulating in the blood include erythrocytes (red blood cells), leukocytes (white blood cells including both B and T cells), non B- and T-lymphocytes, phagocytes, neutrophilic, eosinophilic and basophilic granulocytes, and platelets. These mature cells are derived, on demand, from dividing progenitor cells, such as erythroblasts (for erythrocytes), lymphoid precursors, myeloblasts (for phagocytes including monocytes, macrophages and neutrophils), promyelocytes and myelocytes (for the various granulocytes) and megakaryocytes for the platelets. As stated above, these progenitor cells are themselves derived from precursor stem cells.

A complex network of soluble factors as well as inter- and intra-cellular interactions regulate the proliferation and differentiation of a finite pool of hematopoietic stem cells. Proliferation and differentiation of hematopoietic cells are regulated by hormone-like growth and differentiation factors designated as colony-stimulating factors (CSF) (Metcalf, D. Nature 339, 27–30 (1989)). CSF can be classified into several factors according to the stage of the hematopoietic cells to be stimulated and the surrounding conditions as follows: granulocyte colony-stimulation factor (G-CSF), granulocyte-macrophage colony-stimulation factor (GM-CSF), macrophage colony-stimulation factor (M-CSF), and interleukin 3 (IL-3).

Small amounts of certain hematopoietic growth factors account for the differentiation of stem cells into a variety of blood cell progenitors, for the tremendous proliferation of those cells, and for their differentiation into mature blood cells. For instance, G-CSF participates greatly in the differentiation and growth of neutrophilic granulocytes and plays an important role in the regulation of blood levels of neutrophils and the activation of mature neutrophils (Nagata, S., "Handbook of Experimental Pharmacology", volume "Peptide Growth Factors and Their Receptors", eds. Sporn, M. B. and Roberts, A. B., Spring-Verlag, Heidelberg, Vol.95/1, pp.699–722 (1990); Nicola, N. A. et al., Annu. Rev. Biochem. 58, pp.45–77 (1989)). It is also reported that G-CSF stimulates the growth of tumor cells such as myeloid leukemia cells. (Nicola and Metcalf, Proc. Natl. Acad. Sci. USA, 81, 3765–3769 (1984); Begley et al., Leukemia, 1, 1–8 (1987).) Other growth factors include, erythropoietin (EPO), which is responsible for stimulating the differentiation of erythroblasts into erythrocytes and Macrophage-Colony Stimulating Factor (M-CSF) responsible for stimulating the differentiation of myeloblasts and myelocytes into monocytes.

Growth factors are part of a family of chemical messengers known as the cytokines. Cytokines are among the factors that act upon the hematopoietic system to regulate blood cell proliferation and differentiation. Cytokines are also important mediators of the immune response being secreted by both B and T cells, as well as other various lymphocytes. Cytokines encourage cell growth, promote cell activation, direct cellular traffic, act as messengers between cells of the hematopoietic system, and destroy target cells (i.e., cancer cells). Among the various components involved in the modulation and regulation of the hematopoietic system that cytokines play a role in modulating are the tachykinins.

The tachykinins are immune and hematopoietic modulators that belong to a family of peptides encoded by the preprotachykinin-I (PPT-1) gene (1). The tachykinins can be released in the BM and other lymphoid organs as neurotransmitters or from the resident BM immune cells (2–6). In the BM, PPT-I and other hematopoietic growth factors regulate expression of each other through autocrine and paracrine activities. It is believed that various cytokines induce the expression of the PPT-I gene in BM mesenchymal cells (2). The tachykinin family of peptides exerts pleiotropic functions such as neurotransmission and immune/hematopoietic modulation.

PPT-1 peptides exert both stimulatory and inhibitory hematopoietic effects by interacting with different affinities to the G-protein coupled receptors: NK-1, NK-2 and NK-3 (7). NK-1 and NK-2 expression has been reported in BM cells (8). NK-1 is induced in BM cells by cytokines and other stimulatory hematopoietic regulators. NK-2 is constitutively expressed in BM cells that are unstimulated or stimulated with suppressive hematopoietic regulators. NK-1 and NK-2 are not co-expressed in BM cells because NK-1 induction by cytokines is correlated with the down regulation of NK-2. In BM cells, NK-1 expression requires cell stimulation whereas its expression in neural tissue is constitutive (2, 9, 10). It is believed that a particular cytokine discriminates between the expression of NK-1 and NK-2, which directs the type of BM functions: stimulatory vs. inhibitory (8).

Substance P (SP), the major tachykinin released in the BM, stimulates hematopoiesis through interactions with the neurokinin-1 (NK-1) receptor, which is resident on BM stroma, immune cells and other lymphoid organ cells. Hence, the expression of NK-1 determines the hematopoietic response of the tachykinins. NK-2 inhibits hematopoiesis by interacting with neurokinin-A, another tachykinin encoded for by the PPT-I gene. Recently the present inventors have discovered that the stimulatory effects mediated by NK-1 can be changed to hematopoietic inhibition in the presence of the amino terminal of SP, a fragment found endogenously in the BM due to enzymatic digestion of SP by endogenous endopeptidases. Further, dysregulated expression of the PPT-1 gene has been associated with different pathologies such as cancer (Bost et al., 1992b; Henning et al, 1995; Ho et al., 1996; Michaels, 1998; Rameshwar et al, 1997a).

Under normal circumstances, the BM is able to respond quickly to an increased demand for a particular type of cell. The pluripotential stem cell is capable of creating and reconstituting all the cells that circulate in the blood, including both red and white blood cells and platelets. As stated, progenitor cells that derive from stem cells can replicate and differentiate at an astounding, if not alarming rate. On average, 3–10 billion lymphocyte cells can be generated in an hour. The BM can increase this by 10 fold in response to need. However, in the throes of a diseased state, the BM may not produce enough stem cells, may produce too many stem cells or various ones produced may begin to proliferate uncontrollably. Further complications arise when these stem cells or their associated progenitor are not able to differentiate into the various morphologically recognizable and functionally capable cells circulating in the blood.

Lymphoproliferative syndromes consist of types of diseases known as leukemia and malignant lymphoma, which can further be classified as acute and chronic myeloid or lymphocytic leukemia, Hodgkin's lymphoma, and non-Hodgkin's lymphoma. These diseases are characterized by the uncontrollable multiplication or proliferation of leukocytes (primarily the B-cells) and tissue of the lymphatic system, especially lymphocyte cells produced in the BM and lymph nodes.

Lymphocytes (also called leukocytes) are core components of the body's immune system, which is one of the principal mechanisms by which the body attacks and controls cancers. Lymphocytes, or their derivatives, recognize the foreign antigenic nature of cancer cells or of antibodies associated therewith and attack the cancer cells. Upon exposure to a foreign antigen in the human body, lymphoctes naturally proliferate or multiply to combat the antigen.

There are two broad sub-types of lymphocyte cells. These are known as B and T cells. All of them are derived from the bone marrow but T cells undergo a process of maturation in the thymus gland. Mature lymphocytes all have a similar appearance. They are small cells with a deeply basophilic nucleus and scanty cytoplasm. B and T cells circulate in the blood and through body tissues. B cells primarily work by secreting soluble substances called antibodies. Each B cell is programmed to make one specific antibody. When a B cell encounters its triggering anitgen, it goes through a process wherein it is changed into many large plasma cells. Hence, B cells give rise to plasma cells which secrete a specific immunoglobulin (antibodies). T cells also respond to antigens. Some of them (CD4+) secrete lymphokines that act on other cells, thus regulating the complex workings of the immune response. Others (CD8+, cytotoxic) directly contact infected cells and are able to cause lysis therby destroying the infected cells.

Leukemia and other such B-cell malignancies, such as acute and chronic myeloid and lymphocytic leukemia as well as the B-cell subtype of Hodgkins and non-Hodgkin's lymphoma, are examples of lymphoproliferative syndromes that are significant contributors to cancer mortality. In fact, the majority of chronic lymphocytic leukemias are of B-cell lineage. Freedman, Hematol. Oncol. Clin. North Am. 4:405 (1990).

Leukemia can be defined as the uncontrolled proliferation of a clone of abnormal hematopoietic cells. Leukemias are further typically characterized as being myelocytic or lymphocytic. Myeloid leukemias affect the descendents of the myeloid lineage, where as the lymphocytic leukemias involve abnormalities in the lymphoid lineage. Most B cell leukemias and lymphomas are monoclonal, meaning that all of the related tumor cells are derived from one particular aberrant cell.

Generally, leukemia is a neoplastic disease in which white corpuscle maturation is arrested at a primitive stage of cell development. The disease is characterized by an increased number of leukemic blast cells in the bone marrow and by varying degrees of failure to produce normal hematopoietic cells. The condition may be either acute or chronic. Acute myelocytic leukemia (AML) arises from bone marrow hematopoietic stem cells or their progeny. The term "acute myelocytic leukemia" subsumes several subtypes of leukemia e.g. myeloblastic leukemia, promyelocytic leukemia and myelomonocytic leukemia and is a form of cancer that affects the cells producing myeloid blood cells in the BM. As stated above, myeloid cells are red blood cells, platelets and all white blood cells (which include: neutrophils, monocytes, macrophages, eosinophils and basophils). Primarily, AML involves abnormal white blood cells of the neutrophil type. Production of blood cells is obstructed and immature cells known as "blast cells" accumulate in the bone marrow. These cells are unable to mature and differentiate properly leading to a significant reduction of normal blood cells in the circulation. The accumulation of blast cells in the BM prevents production of other cell types resulting in anemia and low platelet blood counts. Acute lymphocytic leukemia (ALL) arises in lymphoid tissues and ordinarily first manifests its presence in bone marrow. ALL is primarily a form of cancer that affects the lymphocytes and lymphocyte producing cells in the BM.

Chronic myelogenous leukemia (CML) is characterized by abnormal proliferation of immature granulocytes, for example, neutrophils, eosinophils and basophils, in the blood, bone marrow, the spleen, liver and sometimes in other tissues. A large portion of chronic myelogenous leukemia patients develop a transformation into a pattern indistinguishable from the acute form of the disease.

This change is known as the "blast crises". Chronic lymphocytic leukemia (CLL) is a form of leukemia in which there is an excess number of mature, but poorly functioning lymphocytes in the circulating blood. It is to be noted that the rate of production of lymphocytes is not significantly increased and may in fact even be slower than normal. CLL has several phases. In the early phase it characterized by the accumulation of small mature functionally-incompetent malignant B-cells having a lengthened life span. The late stages of CLL are characterized by significant anemia and/or thrombocytopenia.

The two main types of lymphoma are Hodgkin's and non-Hodgkin's lymphoma. Hodgkin's disease is a cancer of the lymphatic system—the network of lymph glands and channels that occurs throughout the body. The defining feature of Hogkin's disease is the presence of a distinctive abnormal lymphocyte called a Reed-Sternberg cell. There are five recognized sub-groups of Hodgkin's disease; these are: lymphocyte rich, nodular sclerosing, mixed cellularity, lymphocyte depleted and nodular lymphocyte predominant (which predominantly affects one isolated lymph node). All other types of lymphoma are collectively known as non-Hodgkin's lymphoma. There are thirty sub-types of non-Hodgkin's type lymphoma.

Traditional methods of treating these B-cell malignancies, which includes chemotherapy and radiotherapy, have limited utility due to toxic side effects. Short-term side effects of chemotherapy may include significant toxicity, extreme nausea, vomiting, and serious discomfort. The long-term side effects may include diabetes, other forms of B-cell malignancies, other forms of cancer, heart, lung or other organ disease, fatal bleeding during remission induction, and myelodysplasia. The short-term side effects of radiotherapy may include extreme nausea, vomiting, serious discomfort, sterility and infertility. The long-term side effects of radiotherapy may include other forms B-cell malignancies, cancer, thyroid gland, spleen or other organ failure. These side effects may be moderated by reduced dosages, however, that increases the risk of remission.

Another traditional method for treating B-cell malignancies includes either BM or stem cell transplantation. However, these procedures are plagued with exorbitant cost and high rates of failure. It is both difficult and costly to locate a sufficient donor and even when one is located, rejection of the transplanted cells often takes place, which in turn can lead to graft versus host disease. Most often, these treatments also include a combination of both chemo and radiotherapies, hence, the concomitant risks involved therein would apply here as well.

There is, therefore, a need for a more non-evasive treatment for lymphoproliferative diseases related to either an increase or decrease in differentiation, as well as uncontrolled proliferation. The present invention involves a novel gene, its antisense polynucleotide sequence, the coded for protein and antibodies immunospecific to the coded for protein. More specifically, the present invention provides pharmaceutical compositions of the novel gene, its antisense sequence, the protein and/or antibodies immunospecific to the protein, that can be used to either increase or decrease lymphocyte differentiation and may be useful in inhibiting white blood cell proliferation.

Hence, the methods of the present invention are useful for the prevention and treatment of lymphoproliferative syndromes such as B-cell related maladies, including but not limited to acute and chronic myeloid and lymphocytic leukemia as well as the B-cell subtype of Hodgkin's and non-Hodgkin's lymphomas. Further, the methods of the present invention can be used to increase the effectiveness of both chemo- and radiotherapy. Further still, the use of monoclonal antibodies, in conjunction with the gene, antisense polynucleotide or protein of the present invention, to direct radionuclides, toxins, or other therapeutic agents offers the possibility that such agents can be delivered at lower dosages, selectively to tumor sites, thus limiting toxicity to normal tissues.

SUMMARY OF THE INVENTION

In summary, the bone marrow (BM) is the major organ where immune cells are derived. Homeostasis in the BM is maintained by inter- and intra-cellular interactions by the various subsets of BM cells. An understanding of normal BM functions has been extended to unravel a novel mechanism of BM-derived diseases such as leukemia and lymphoma. The present invention discloses the cloning of a new cDNA from stimulated BM stromal cells that was retrieved with a probe specific for the neurokinin-1 (NK-1) receptor. The cloned cDNA was designated 'Hematopoietic Growth Factor Inducible Neurokinin-1 type' (HGFIN) gene based on its expression in differentiated hematopoietic cells, undetectable levels in the corresponding progenitors, and the concomitant down regulation of Id2, an inhibitor of cell differentiation.

Based on the methods of the present invention it has been determined given that HGFIN expression is down regulated in differentiated cells that were stimulated with a mitogen (LPS), HGFIN can be an inhibitor of cell activation. This is in contrast to its effect in mesenchymal BM cells in which HGFIN is induced by cytokines and a neurotrophic factor. Since BM mesenchymal cells support hematopoiesis and are involved in bone remodeling, these data show that HGFIN can be involved in BM functions throughout the hematopoietic hierarchy.

These discoveries have led to the compositions and methods of the present invention. Hence, the present invention provides a novel gene, HGFIN, which encodes a protein receptor that is involved in the regulation of hematopoietic proliferation and differentiation, and may act as a negative regulator of the Id2 protein. The protein of the present invention may be involved as a central mediator of white blood cell, progenitor, differentiation, and therefore, may be useful in the prevention and treatment of lymphoproliferative syndromes such as B-cell related maladies, including but not limited to acute and chronic myeloid and lymphocytic leukemia as well as the B-cell subtype of Hodgkin's and non-Hodgkin's lymphomas.

According to one aspect of this invention, an isolated polynucleotide encoding a novel white blood cell regulating protein is provided. Preferably, the polynucleotide comprises the sequence: SEQ ID NO:1; an allelic variant of SEQ ID NO:1; a sequence hybridizing with SEQ ID NO:1 or its complement under moderate hybridization and washing conditions; an antisense sequence to SEQ ID NO:1; a sequence encoding a polypeptide having an amino acid sequence of SEQ ID NO:2 with up to 30% conservative substitutions; SEQ ID NO:2; an allelic variant of SEQ ID NO:2 and a sequence hybridizing with SEQ ID NO:2 or its complement under moderate hybridization and washing conditions.

Another aspect of the invention features a recombinant DNA or RNA molecule comprising a vector having an insert that includes part or all of an HGFIN, or its antisense, polynucleotide and cells transformed with the recombinant DNA molecule. Preferably, the cells are murine, human, bovine, canine, feline or rat cells. Most preferably, the cells are BM derived cells, such as stem cells, progenitor cells, white and/or red blood cells, including B-cells, T-cells, granulocytes, monocytes, macrophages, neutrophils, and the like, of the aforementioned organisms.

The invention also features an isolated polypeptide produced by expression of the HGFIN polynucleotides described above. Antibodies immunologically specific for the protein, or one or more epitopes thereof, are also provided. Pharmaceutically compositions containing the HGFIN polynucleotide, antisense sequence, protein, protein fragments and/or antibodies immunospecific to the protein, are also provided.

The present invention may be implicated in diseases and conditions such as leukemia and lymphoma. Hence, the invention relates to compositions and methods for treating diseases associated with increased cell proliferation, by administering a HGFIN gene or protein to increase differentiation, and treating a disease associated with decreased cell proliferation by administering an HGFIN antisense sequence, thereby downregulating the expression of the HGFIN protein, or antibody to competitively inhibit the SP modulator, or any other natural or synthetic ligand for HGFIN, from binding to the HGFIN receptor and inducing cell differentiation.

In a more specific embodiment, the invention relates to methods for using such polynucleotides, polypeptides and antibodies for preventing or treating acute and chronic myeloid leukemia and acute and chronic lymphocytic leukemia, as well as the B-cell subtype of Hodgkin's and non-Hodgkin's lymphomas. More specifically, for example, the compositions of the present invention may be used for the treatment of Acute Myelocytic Leukemia, which is associated with the accumulation of immature blast cells, wherein the administration of HGFIN compositions may enhance the maturation of the affected cells thus alleviating the leukemic condition and the anemia and low platelet blood count associated with this disease. Further, the compositions of the present invention may also be useful in the treatment of Acute Lymphocytic Leukemia which is associated with increased proliferation of immature lymphocytes, wherein the administration of an HGFIN composition may inhibit and or slow down proliferation and promote differentiation, helping the cells mature before becoming the cells of the peripheral blood system.

The compositions of the present invention may also be useful in the treatment of Chronic Myelogenous Leukemia which is marked by the abnormal proliferation of immature granulocytes in the BM and blood, wherein the administration of an HGFIN composition that includes an HGFIN antisense sequence or HGFIN immunospecific antibody may inhibit and or slow down proliferation, allowing the developing cells time to mature before differentiating into the cells of the peripheral blood system. Further, the compositions of the present invention may also be useful in the treatment of Chronic Lymphocytic Leukemia which is marked by mature but poorly functioning lymphocytes circulating in the blood, wherein the administration of an HGFIN composition may inhibit and or slow down the earlier stages of proliferation, allowing more time for the cells to mature before terminal differentiation.

In the same way, the compositions and methods of the present invention may be useful in the treatment of both Hodgkin's and non-Hodgkin's type Lymphoma, which can be marked both by lymphocytic rich and lymphocytic depleted blood levels.

In another embodiment HGFIN immunospecific antibodies may be used to target disease cells, these antibodies may also be conjugated with chemo- or radio-toxic agents to kill off leukemia or lymphoma associated cells. Such a method would also allow for the reduction of side effects caused by the administration of such cyto- or radio-toxic elements by reducing the amount of dosage of the toxic agent needed to kill affected cells.

BRIEF DESCRIPTION OF THE DRAWINGS

The invention is best understood from the following detailed description when read in connection with the accompanying drawings, in which:

FIG. 1 cDNA sequence of HGFIN, Accession number AF322909. Open reading frame finder using six frames indicated that sequences +60/+1742 as the most probable coding sequence.

FIG. 2 is a diagram of the putative structure for HGFIN protein based on information provided by PredictProtein. A. Spatial arrangement of the HGFIN protein within a lipid bilayer. B. Sequence annotation for regions within the HGFIN protein.

FIG. 5 shows expression of HGFIN in differentiated and undifferentiated BM cells. HGFIN expression was studied by northern analyses with total RNA from the following tissues: A. BMNC, B. PBMC, C. BMNC cultured with G-CSF or M-CSF to differentiation or termination of culture before differentiation. FIGS. A and B: Each lane represents a different BM donor. Arrows in FIG. C show a different BM donor. C: Lane 1, M-CSF-differentiated cells; Lane 2, G-CSF-differentiated cells; Lane 3, media alone; Lane 4, G-CSF or M-CSF-undifferentiated cells. Cytochemical staining verified cell differentiation.

DETAILED DESCRIPTION OF THE INVENTION

Introduction

Figure 3:
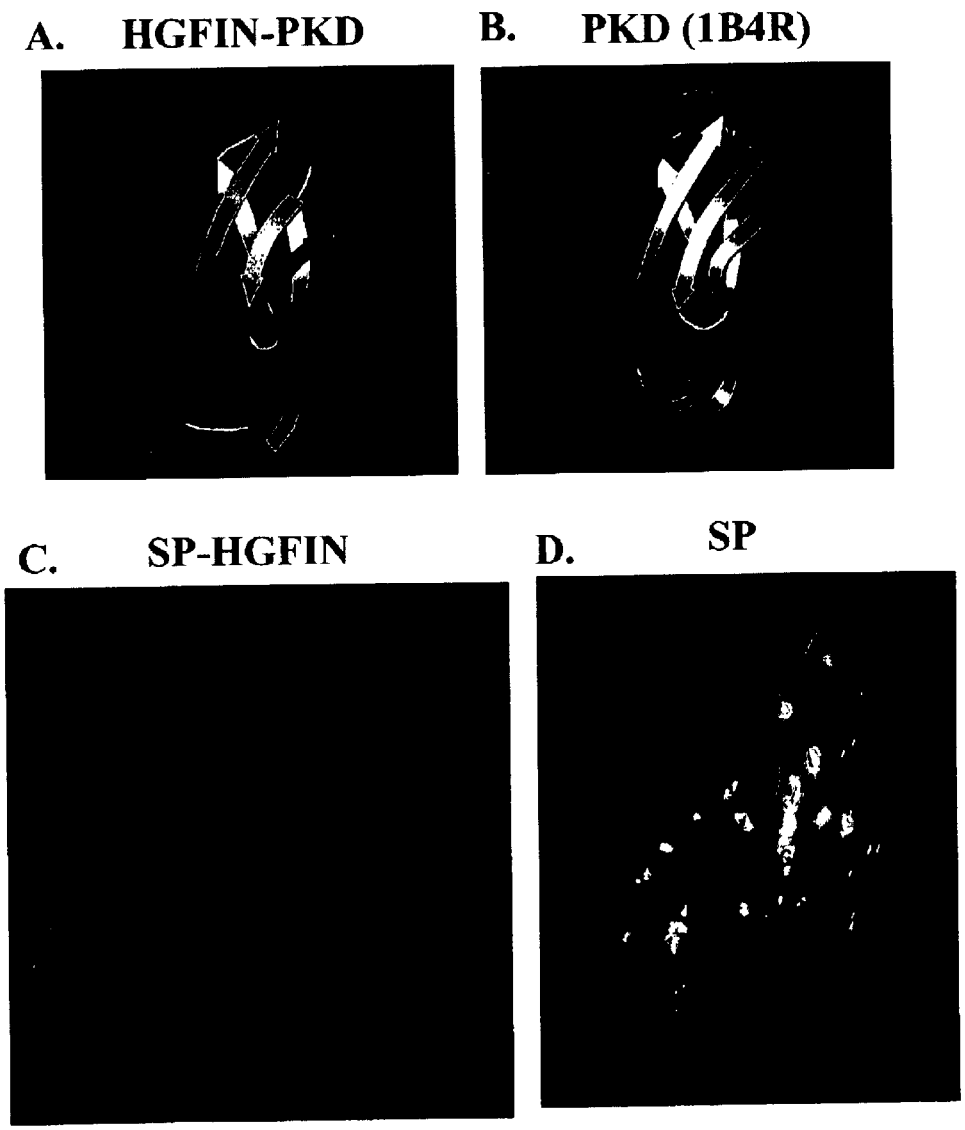
FIG. 3 is a 3-D structure of the polycistic kidney disease (PKD) consensus sequence within HGFIN with an interactive ligand. The NMR pattern for the PKD region (PD 1B4R) was used to generate a 3-D model for the homologous region within HGFIN. Ribbon structure for the PKD within HGFIN (A) is compared with the structure in the protein database (1B4R) (B). Docking of PKD from HGFIN and SP by the electrostatic potential of the solvent accessible surfaces (C). The physical properties for the 3-D structure of SP shows hydrophilic (blue) and liphophilic regions (brown).

Applicants have identified Hemtaopoietic Growth Factor Inducible Neurokinin-I type (HGFIN) as a gene that is differentially regulated between differentiated peripheral hematopoietic cells and immature, unstimulated mesenchymal stromal cells. Applicants have performed differential cloning between mature, differentiated leukocytes and immature, unstimulated stromal cells and have identified the HGFIN gene by DNA sequence analysis. Based on an understanding of the leukemia and lymphoma related diseases, in which uncontrolled proliferation of immature progenitor cells without differentiation is indicative of the diseased state, the genes and or proteins of the present invention may play a role in mediating the initiation and progression of B-cell related blood diseases, specifically, the various related leukemias and lymphomas.

Bone marrow (BM) is the major organ where immune cells are derived. Homeostasis in the BM is maintained by inter- and intra-cellular interactions by the various subsets of BM cells. An understanding of normal BM functions has begun to unravel the mechanisms of BM-derived diseases such as leukemia and lymphoma. The present invention relates to the cloning of a cDNA from stimulated BM stromal cells that was retrieved with a probe specific for the neurokinin-1 (NK-1) receptor. NK-1 mediates hematopoietic regulation by interacting with ligands that belong to the tachykinin family. The cloned cDNA was designated 'Hematopoietic Growth Factor Inducible Neurokinin-1 type' (HGFIN) gene based on its expression in differentiated hematopoietic cells, undetectable levels in the corresponding progenitors, and the concomitant down regulation of Id2, an inhibitor of cell differentiation.

From the methods, herein described, it has been determined that based on the fact that HGFIN expression was down regulated in differentiated cells that were stimulated with a mitogen (LPS) HGFIN could be an inhibitor of cell activation. Further, in mesenchymal BM cells, HGFIN was induced by both cytokines and a neurotrophic factor. Since the BM mesenchymal cells support hematopoiesis and are involved in bone remodeling, these data indicate that HGFIN is likely involved in BM functions throughout the hematopoietic hierarchy.

To understand the difference in NK-1 function in the BM, three different cDNA libraries were screened with an NK-1-specific probe (11). Seven clones were selected after the cDNA libraries were screened with a cDNA probe specific for the human NK-1 (11). After sequencing the DNA inserts in the forward and reverse orientations, search of the DNA database indicated that Clone 7 was homologous to the mnb cDNA (27) and that the coding region spanned +60/+1742 (FIG. 1).

Since the mesenchymal/stromal cells were the major NK-1-expressing cell subsets (2), two of the cDNA libraries were prepared with cytokine-stimulated BM stroma. A cDNA library from unstimulated BM mononuclear cells was also screened for the purpose of identifying NK-1 subtypes in baseline/unstimulated cells. One of the retrieved clones was sequenced and its expression in various tissues was studied. HGFIN expression was different at the various cellular levels that comprise the hematopoietic hierarchy. At the lower spectrum, HGFIN mRNA was detected in differentiated hematopoietic cells and in peripheral immune cells, which are predominantly differentiated cells. In contrast, HGFIN mRNA was undetectable in unstimulated, mesenchymal stromal cells unless they were stimulated. The stromal cells are involved in the hematopoietic spectrum at all levels, in particular at the stem cell and osteoclast development (12–14) levels. Thus, the expression of HGFIN in the stromal cells leads to the conclusion that the HGFIN gene is involved in the support of hematopoiesis at various stages, and might also be involved in bone remodeling (13, 14). Further evidence for HGFIN as a mediator of cell differentiation was shown when its expression coincided with the down regulation of Id2, the transcription factor that is a dominant negative regulator of cell differentiation (15). Other functions of HGFIN were suggested by its down regulation in immune cells following cell activation. Computational analyses provided insights into the properties of HGFIN protein. For further details, see the examples detailed herein below.

Although specific embodiments of the present invention will now be described, it should be understood that such embodiments are by way of example only and merely illustrative of but a small number of the many possible specific embodiments that can represent applications of the principles of the present invention. Various changes and modifications obvious to one skilled in the art to which the present invention pertains are deemed to be within the spirit, scope and contemplation of the present invention as further defined in the appended claims.

Definitions

Various terms relating to the biological molecules of the present invention are used throughout the specification and claims.

"HGFIN" refers generally to an HGFIN polypeptide that is highly inducible by NK-1 stimulation in differentiated hematopoietic cells and also in peripheral immune cells, as well as having expression that coincides with the down regulation of Id2, in accordance with the present invention, which is described in detail herein above and throughout the specification.

"HGFIN activity or HGFIN polypeptide activity" or "biological activity of the HGFIN or HGFIN polypeptide" refers to the metabolic or physiologic function of said HGFIN including similar activities or improved activities or these activities with decreased undesirable side effects. Also included are antigenic and immunogenic activities of said HGFIN. In particular, HGFIN encodes a protein receptor that has homology at its C-terminal to PKD and may bind to SP.

"HGFIN gene" refers to a polynucleotide as defined above in accordance with the present invention, which encodes an HGFIN polypeptide.

An "HGFIN therapeutic" refers to a therapeutically effective amount of an HGFIN related genetic sequence such as, but not limited to polynucleotide, polynucleotide antisense sequence, and HGFIN peptide, protein or protein fragment as well as a HGFIN antibody or antibody fragment.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA.

The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the gene-encoded amino acids. "Polypeptides" include amino acid sequences modified either by natural processes, such as posttranslational processing, or by chemical modification techniques that are well known in the art. Such modifications are well described in basic texts and in more detailed monographs; as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods.

Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cystine, formation of pyroglutamate, formylation, gamma-carboxylation, glycosylation, GPI anchor formation, hydroxylation, iodination, metbylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins—Structure And Molecular Properties, 2nd Ed.*, T. E. Creighton, W. H. Freeman and Company, New York, 1993 and Wold, F., *"Posttranslational Protein Modifications: Perspectives and Prospects*, pgs. 1–12 in *"Posttranslational Covalent Modification Of Proteins"*, B, C. Johnson, Ed., Academic Press, New York, 1983; Seifter et al., *"Analysis for protein modifications and nonprotein cofactors"*, Meth Enzymol (1990) 182:626–646 and Rattan et al., *"Protein Synthesis: Posttranslational Modifications and Aging"*, Ann AIY Acad Sci (1992) 663:48–62. "Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical.

A variant and reference polypeptide may differ in amino acid sequence by one or more substitutions, additions, and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. For instance, a conservative amino acid substitution may be made with respect to the amino acid sequence encoding the polypeptide. A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "substantially the same" refers to nucleic acid or amino acid sequences having sequence variation that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, *J. Theor. Biol. H* 9:205). When referring to nucleic acid-molecules, "percent identical" refers to the percent of the nucleotides of the subject nucleic acid sequence that have been matched to identical nucleotides by a sequence analysis program.

"Identity" and "similarity" can be readily calculated by known methods. Nucleic acid sequences and amino acid sequences can be compared using computer programs that align the similar sequences of the nucleic or amino acids thus define the differences. In preferred methodologies, the-BLAST programs (NCBI) and parameters used therein are employed, and the DNAstar system (Madison, Wis.) is used to align sequence fragments of genomic DNA sequences. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

With respect to oligonuelcotide constructs, but not limited thereto, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide construct with a substantially complementary sequence contained within a single-stranded DNA or RNA molecule of the invention, to the substantial exclusion of hybridization of the oligonucleotide with single-stranded nucleic acids of non-complementary sequence.

The term "substantially pure" refers to a "preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate to the compound of interest (e.g. chromatographic methods, agarose or polyacrylamide gel electrophoresis, HPLC analysis, and the like).

The term "expression cassette" refers to a nucleotide sequence that contains at least one coding sequence along with sequence elements which direct the initiation and termination of transcription. An expression cassette may include additional sequences, including, but not limited to promoters, enhancers, and sequences involved in post-transcriptional or posttranslational processes.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA". Such a nucleic acid construct may contain a coding sequence for a gene product of interest, along with a selectable marker gene and/or a reporter gene.

The term "selectable marker gene" refers to a gene encoding a product that, when expressed, confers a selectable phenotype such as antibiotic resistance on a transformed cell.

The term "reporter gene" refers to a gene that encodes a product that is detectable by standard methods, either directly or indirectly.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The term "DNA construct", as defined above, is also used to refer to a heterologous region, particularly one constructed for use in transformation of a cell. A cell has been "transformed" or "transfected" or "transduced" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

The term "in vivo delivery" involves the use of any gene delivery system, such as viral- and liposome-mediated transformation for the delivery and introduction of a therapeutic agent to the cells of a subject while they remain in the subjectSuch therapeutic agents may include, for example, HGFIN DNA, cDNA, RNA, and antisense polynucleotide sequences.

As used herein, the term "transduction," is used to describe the delivery of DNA to eukaryotic cells using viral mediated delivery systems, such as, adenoviral, AAV, retroviral, or plasmid delivery gene transfer methods. Preferably the viral mediated delivery system is targeted specifically to the cell, wherein delivery is sought. The production of targeted delivery systems is well known and practiced in the recombinant arts. A number of methods for delivering therapeutic formulations, including DNA expression constructs (as described further below), into eukaryotic cells are known to those skilled in the art. In light of the present disclosure, the skilled artisan will be able to deliver the therapeutic agents of the present invention to cells in many different but effective ways. For instance, the specificity of viral gene delivery may be selected to preferentially direct the HGFIN gene to a particular target cell, such as by using viruses that are able to infect particular cell types (i.e., leukemia cells). Naturally, different viral host ranges will dictate the virus chosen for gene transfer.

"In vitro gene delivery" refers to a variety of methods for introducing exogenous DNA into a cell that has been removed form its host environment.

As used herein the term, "transfection" is used to describe the delivery and introduction of a therapeutic agent to a cell using non-viral mediated means, these methods include, e.g., calcium phosphate- or dextran sulfate-mediated transfection; electroporation; glass projectile targeting; and the like. These methods are known to those of skill in the art, with the exact compositions and execution being apparent in light of the present disclosure.

Ex vivo gene delivery" refers to the procedure wherein appropriate cells are removed form the host organism, transformed, transduced or transfected in accordance with the teachings of the present invention, and replaced back into the host organism, for the purpose of therapeutic restoration and/or prevention.

Delivery of a therapeutic agent" may be carried out through a variety of means, such as by using parenteral delivery methods such as intravenous and subcutaneous injection, and the like. Such methods are known to those of skill in the art of drug delivery, and are further described herein in the sections regarding pharmaceutical preparations and treatment. Compositions, include pharmaceutical formulations, comprising a HGFIN gene, protein, or antisense polynucleotide sequence that may be delivered in combination with a radio or chemotoxic agent, such as cisplatin. In such compositions, the HGFIN may be in the form a DNA segment, recombinant vector or recombinant virus that is capable of expressing a HGFIN protein in a cell; specifically, a BM cell. These compositions, including those comprising a recombinant viral gene delivery system, such as an adenovirus particle, may be formulated for in vivo administration by dispersion in a pharmacologically acceptable solution or buffer. Preferred pharmacologically acceptable solutions include neutral saline solutions buffered with phosphate, lactate, Tris, and the like.

A "clone" is a population of cells derived from a single cell or common ancestor by mitosis.

A "cell line" is a clone of a primary cell that is capable of stable growth in vitro for many generations.

The term "contacted" when applied to a cell is used herein to describe the process by which an HGFIN gene, protein or antisense sequence, and/or an accessory element (such as a an antibody or cytotoxic agent), is delivered to a target cell or is placed in direct proximity with the target cell. This delivery may be in vitro or in vivo and may involve the use of a recombinant vector system. Any method may be used to contact a cell with the HGFIN associated protein or nucleotide sequence, so long as the method results in either increased or decreased levels of functional HGFIN protein within the cell. This includes both the direct delivery of an HGFIN protein to the cell and the delivery of a gene or DNA segment that encodes HGFIN, or its antisense polynucleotide sequence, which gene or antisense sequence will direct or inhibit, respectfully, the expression and production of HGFIN within the cell. Since protein delivery is subject to drawbacks, such as degradation and low cellular uptake, it is contemplated that the use of a recombinant vector that expresses a HGFIN protein, or encodes for an HGFIN polynucleotide antisense sequence, will be of particular advantage for delivery.

The term "mammal" refers to such organisms as mice, rats, rabbits, goats, horse, sheep, cattle, cats, dogs, pigs, more preferably monkeys and apes, and most preferably humans.

"Antibodies" as used herein includes polyclonal and monoclonal antibodies, chimeric, single chain, and humanized antibodies, as well as Fab fragments, including the products of a Fab or other immunoglobulin expression library. With respect to antibodies, the term, "immunologically specific" refers to antibodies that bind to one or more epitopes of a protein of interest, but which do not substantially recognize and bind other molecules in a sample containing a mixed population of antigenic biological molecules.

The term "specific binding affinity" is meant that the antibody or antibody fragment binds to target compounds with greater affinity than it binds to other compounds under specified conditions. Antibodies or antibody fragments having specific binding affinity to a compound may be used in methods for detecting the presence and/or amount of the compound in a sample by contacting the sample with the antibody or antibody fragment under conditions such that an immunocomplex forms and detecting the presence and/or amount of the compound conjugated to the antibody or antibody fragment.

The term "polyclonal" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique that provides for the production of antibody molecules by continuous cell lines in culture. Monoclonal antibodies may be obtained by methods known to those skilled in the art. See, for example, Kohler, et al., Nature 256:495–497, 1975, and U.S. Pat. No. 4,376, 110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the target compound. The term "antibody fragment" also includes single charge antibodies.

With respect to "therapeutically effective amount" is an amount of the polynucleotide, antisense polynucleotide or protein of HGFIN, or immunospecific antibody, or fragment thereof, that when administered to a subject is effective to bring about a desired effect (e.g., an increase or decrease in cell maturation, differentiation and/or proliferation) within the subject.

With respect to "radio" or "chemotherapy agents," these terms are defined herein as any chemical compound or treatment method that induces cell damage and/or results in death of a cell, when applied. Such agents and factors include adriamycin, 5-fluorouracil (5FU), etoposide (VP-116), camptothecin, actinomycin-D, mitomycin C, cisplatin (CDDP), and even hydrogen peroxide. Other factors include radiation and waves, such as γ-irradiation, X-rays, UV-irradiation, microwaves, electro-emissions, and the like. The invention also encompasses the use of a combination of one or more of these agents used in concert, whether radiation-based or actual compounds, such as the use of X-rays with cisplatin.

Polynucleotides

The present invention provides a novel gene, HGFIN, which may act as a mediator of pluripotent stem or progenitor cell differentiation and other interrelated physiological processes of hematopoieses. The HGFIN gene and protein of the present invention share a portion of sequence homology to the polycistic kidney disease (PKD) portion of the NK-1 receptor. Hence, like NK-1, the coded for HGFIN protein binds Substance P (SP) and thus plays a role in the stimulation of hematopoiesis and/or, as determined from the methods described herein, HGFIN may be instrumental in the regulation of leukocyte proliferation and differentiation, including the inducement of differentiation and inhibition of proliferation. The summary of the invention described above is non-limiting and other features and advantages of the invention will be apparent from the following detailed description.

The present invention concerns compositions and methods for treating various lymphoproliferative related diseases associated with either an unhealthy increase or decrease in leukocyte proliferation and/or differentiation. The invention is based firstly on the inventor's discovery that HGFIN mRNA was detected in differentiated hematopoietic and peripheral immune cells but not in unstimulated mesesnchymal stromal cells, and secondly on the proteomic analyses that show that SP binds to the PKD portion of the HGFIN protein receptor. Thus, the present inventors discovered that HGFIN plays a role in hematopoietic cell maturation and may be useful in the treatment of the various forms of leukemia, lymphoma and other maladies related to stem and/or progenitor cell proliferation or differentiation.

As stated, this invention is based in part on the discovery that HGFIN mRNA was detected in differentiated hematopoietic cells and in peripheral immune cells, which are predominantly differentiated cells. In contrast, HGFIN mRNA was undetectable in unstimulated, mesenchymal stromal cells unless they were stimulated. Since, the stromal cells regulate the hematopoietic spectrum at all levels, in particular with regard to stem cell and osteoclast development (12–14), the expression of HGFIN in the stromal cells suggests that the HGFIN gene plays a role in the support of hermatopoiesis at various stages, and is likely to be involved in bone remodeling (13, 14). Further evidence for HGFIN as a mediator of cell differentiation was shown when its expression coincided with the down regulation of Id2, the transcription factor that is a dominant negative regulator of cell differentiation (15). Other functions of HGFIN were suggested by its down regulation in immune cells following cell activation.

As described in detail in Example 1, the HGFIN gene was first identified and cloned from human BM stroma cells. The human HGFIN gene is set out in SEQ ID NO:1. The nucleic acid sequence of the HGFIN cDNA was translated in six reading frames. Computer analysis of the protein sequence, using PredictProtein software, showed that the longest and most probable protein consisted of 560 residues. A BLAST search indicated homology to the mub precursor protein (SwissProt Q14956). This 560 amino acid protein was aligned to the sequence of the NK-1 receptor. PredictProtein results were used to determine the characteristics of the HGFIN protein. Among the databases used by PredictProtein were ProSite, ProDom, Predator, Globe and PHD (21–25). GeneMine's Look 3.5 (Molecular Ass. Group) was used to construct a 3-D model of a region of the HGFIN protein. TRIPOS Sybyl was used to minimize the 3-D structure and also examine the possible interaction with SP.

The HGFIN polynucleotides of the present invention include isolated polynucleotides encoding the HGFIN polypeptides and fragments, and polynucleotides closely related thereto. More specifically, HGFIN polynucleotides of the invention include a polynucleotide comprising the human nucleotide sequences contained in SEQ ID NO:1 encoding an HGFIN polypeptide of SEQ ID NO:2, and polynucleotides having the particular sequence of SEQ ID NO:1.

HGFIN polynucleotides further include a polynucleotide comprising a nucleotide sequence that has at least 70% identity over its entire length to a nucleotide sequence encoding the HGFIN polypeptide of SEQ ID NO:2, and a polynucleotide comprising a nucleotide sequence that is at least 70% identical to that of SEQ ID NO: 1, over its entire length. In this regard, polynucleotides with at least 70% are preferred, more preferably at least 80% even more preferably at least 90% identity, yet more preferably at least 95% identity, 97% are highly preferred and those with at least 98–99% are most highly preferred, with at least 99% being the most preferred. Also included under HGFIN polynucleotides are a nucleotide sequence which has sufficient identity to a nucleotide sequence contained in SEQ ID NO:1, to hybridize under conditions useable for amplification or for use as a probe or marker. The invention also provides polynucleotides that are complementary to such HGFIN polynucleotides.

Also included in the present invention are polynucleotides encoding polypeptides which have at least 70% identity, preferably at least 80% identity, more preferably at least 90% identity, yet more preferably at least 95% identity, even more preferably at least 97–99% identity, to the amino acid sequence of SEQ ID NO:2, over the entire length of the recited amino acid sequences.

The nucleotide sequences encoding the HGFIN polypeptide of SEQ ID NO:2 may be identical to the polypeptide encoding sequence contained in SEQ ID NO:1, or it may be a sequence, which as a result of the redundancy (degeneracy) of the genetic code, also encodes the polypeptide of SEQ ID NO:2.

When the polynucleotides of the invention are used for the recombinant production of the HGFIN polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. The polynucleotide may also contain non-coding 5' and 3' sequences, such as transcribed, non-translated sequences, splicing and polyadenylation signals, ribosome binding sites and sequences that stabilize mRNA.

Thus, this invention provides oligonucleotides (sense or antisense strands of DNA, cDNA or RNA) having sequences capable of hybridizing with at least one sequence of a nucleic acid molecule encoding the protein of the present invention. Such oligonucleotides are useful as probes for detecting HGFIN genes or transcripts and may also be useful in the treatment of various blood cell related diseases, when delivered by an appropriate vehicle to the affected cells. In one preferred embodiment, oligonucleotides for use as probes or primers are based on rationally-selected amino acid sequences chosen from SEQ ID NO:1. In preferred embodiments, the amino acid sequence information is used to make degenerate oligonucleotide sequences as is commonly done by those skilled in the art which can be used to screen cDNA libraries from human, mouse, bovine, canine, feline and rat.

HGFIN polynucleotides of the present invention may be prepared by two general methods: (1) they may be synthesized from appropriate nucleotide triphosphates, or (2) they may be isolated from biological sources. Both methods utilize protocols well known in the art. The availability of nucleotide sequence information, such as the cDNA having SEQ ID NO:1, enables preparation of an isolated nucleic acid molecule of the invention by oligonucleotide synthesis.

Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

HGFIN genes also may be isolated from appropriate biological sources using methods known in the art. In the exemplary embodiment of the invention, HGFIN may be isolated from genomic libraries of human, mouse, bovine or rat. In alternative embodiments, cDNA clones of HGFIN may be isolated, such as what has been isolated from human, for instance from: murine, bovine and rat cDNA libraries. A preferred means for isolating HGFIN genes is PCR amplification using genomic or cDNA templates and HGFIN specific primers. Genomic and cDNA libraries are commercially available, and can also be made by procedures well known in the art. In positions of degeneracy where more than one nucleic acid residue could be used to encode the appropriate amino acid residue, all the appropriate nucleic acid residues may be incorporated to create a mixed oligonucleotide population, or a neutral base such as inosine may be used. The strategy of oligonucleotide design is well known in the art.

Alternatively, PCR primers may be designed by the above method to match the coding sequences of a human, murine, bovine, or rat protein and these primers used to amplify the native nucleic acids from isolated cDNA or genomic DNA.

In accordance with the present invention, nucleic acids having the appropriate level sequence homology (i.e., 70% identity or greater) with part or all the coding regions of SEQ ID NO:1 may be identified by using hybridization and washing conditions of appropriate stringency. For example, hybridizations may be performed, according to the method of Sambrook et al., using a hybridization solution comprising: 1.0% SDS, up to 50% formamide, 5×SSC (150 mM NaCl, 15 mM trisodium citrate), 0.05% sodium pyrophosphate (pH 7.6), 5× Denhardt's solution, and 100 microgram/ml denatured, sheared salmon sperm DNA. Hybridization is carried out at 37–42° C. for at least six hours. Following hybridization, filters are washed as follows: (1) 5 minutes at room temperature in 2× SSC and 1% SDS; (2) 15 minutes at room temperature in 2×SSC and 0.1% SDS; (3) 30 minutes to 1 hour at 37° C. in 2×SSC and 0.1% SDS; (4) 2 hours at 45–55° C. in 2×SSC and 0.1% SDS, changing the solution every 30 minutes.

One common formula for calculating the stringency conditions required to achieve hybridization between nucleic acid molecules of a specified percent identity is set forth by (Sambrook et al., 1989, supra):

$$T_m = 81.5° C. + 16.6 \text{ Log}[Na+] + 0.41(\% G-C) - 0.63(\% \text{ formamide}) - 600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20–25° C. below the calculated $T_m$ of the of the hybrid. Wash conditions should be as stringent as possible for the degree of identity of the probe for the target. In general, wash conditions are selected to be approximately 12–20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and wash in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and wash in 1×SSC and 0.5% SDS at 6–5° C. for 15 minutes. Very high stringency hybridization is defined as hybridization in 6×SSC, 5× Denhardt's solution, 0.5% SDS and 100 µg/ml denatured salmon sperm DNA at 42° C., and wash in 0.1×SSC and 0.5% SDS at 65° C. for 15 minutes.

Nucleic acids of the present invention may be maintained as DNA in any convenient cloning vector. In a preferred embodiment, clones are maintained in plasmid cloning/expression vector, such as pBluescript (Stratagene, La Jolla, Calif.), that is propagated in a suitable *E. coli* host cell.

The HGFIN polynucleotides may be used for a variety of purposes in accordance with the present invention. DNA, cDNA or RNA, or fragments thereof may be used as probes to detect the presence of and/or expression of HGFIN genes. Methods in which HGFIN nucleic acids may be utilized as probes for such assays include, but are not limited to: (1) in situ hybridization; (2) Southern hybridization (3) Northern hybridization; and (4) assorted amplification reactions such as polymerase chain reaction (PCR).

The HGFIN nucleic acids may also be utilized as probes to identify related genes from other species. As is well known in the art, hybridization stringencies may be adjusted to allow hybridization of nucleic acid probes with complementary sequences of varying degrees of homology.

As described above, HGFIN nucleic acids may be used to produce large quantities of substantially pure HGFIN proteins, or selected portions thereof.

The HGFIN nucleic acids of the present invention can be used to identify and isolate other members involved in the hematopoietic response to various members of the tachykinin family, in which HGFIN may be involved. A yeast two-hybrid system can be used to identify proteins that physically interact with the HGFIN protein, as well as isolate their nucleic acids. In this system, the coding sequence of the protein of interest is operably linked to the coding sequence of half of an activator protein. This construct is used to transform a yeast cell library that has been transformed with DNA constructs that contain the coding sequence for the other half of the activator protein operably linked to a random coding sequence from the organism of interest. When the protein made by the random coding sequence from the library interacts with the protein of interest, the two halves of the activator protein are physically associated and form a functional unit that activates the reporter gene.

In accordance with the present invention, all or part of the human HGFIN coding sequence may be operably linked to the coding sequence of the first half of the activator, and the library of random coding sequences may be constructed with cDNA from human and operably linked to the coding sequence of the second half of the activator protein. Several activator protein/reporter genes are customarily used in the yeast two hybrid system, the Gal4/LacZ system (see Clark et al., 1998 *PNAS* 95:5401–5406), among others.

The nucleotide sequences of the present invention are also valuable for chromosome localization. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. The relationship between genes and diseases that have been mapped to the same chromosomal region are then identified through linkage analysis (co-inheritance of physically adjacent genes).

Polypeptides

In one aspect, the present invention relates to human HGFIN polypeptides (or HGFIN proteins). The human HGFIN polypeptides include the polypeptide of SEQ ID NO:2; as well as polypeptides comprising the amino acid sequence of SEQ ID NO:2; and polypeptides comprising the amino acid sequences which have at least 70% identity to that of SEQ ID NO:2, over its entire length. Preferably HGFIN polypeptide exhibit at least one biological activity of HGFIN. The present invention further provides for a polypeptide which comprises an amino acid sequence which has at least 80% identity, more preferably at least 90% identity, yet more preferably at least 95% identity, most preferably at least 97–99% identity, to that of SEQ ID NO:2 over the entire length of SEQ ID NO:2.

As stated above, the HGFIN gene and protein of the present invention share a portion of sequence homology to the PKD portion of the NK-1 receptor. The HGFIN coding sequence predicted that the most probable translational product was equivalent to 560 residues. Based on the results of ProSite, the HGFIN protein contains several stretches of glycosylated residues in the extracellular portion (FIG. 2). Both TMHMM (25) and PHDhtm. (23, 24) programs predicted that residues 485–508 are transmembrane. TMHMM suggests that residues 1–485 are extracellular, and residues 509–560 are intracellular.

General structural analysis of HGFIN through Predict-Protein gained further insights on the characteristics and molecular structure (FIG. 2A). Based on GLOBE analyses, the binding domain is predicted to be compact rather than extended. Predator analysis indicated that the extracellular domain consists mainly of extended sheets and loops. There are at least two distinct regions that are thought to form the binding domain (FIG. 2A, extracellular region). The results of structural analysis through PredictProtein matched information from SwissProt on the characteristics of nmb (Accession Q14956), which is 97% homologous to HGFIN. According to ProDom, a large stretch of the extracellular region of HGFIN is homologous to the PMEL-17 class of proteins found in polycystic kidney disorder (28). One important structural region of these proteins is the PKD region, whose structure is available in the RCSB protein database. The homologous region within HGFIN (FIG. 3A) has been modeled from the PKD region of polycystein-1 (IB4R) (FIG. 3B). The 3-D model of the PKD region within HGFIN was constructed using GeneMine Look 3.5 homology modeling algorithm.

The HGFIN polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the HGFIN polypeptides are also included in the invention. A fragment is a polypeptide having an amino acid sequence that entirely is the same as part, but not all, of the amino acid sequence of the aforementioned HGFIN polypeptides. Preferred fragments include, for example, truncation polypeptides having the amino acid sequence of HGFIN polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate HGFIN activity, including those with a similar activity or an improved activity, or with a decreased undesirable activity. Also included are those that are antigenic or immunogenic in an animal, especially in a human.

Preferably, all of these polypeptide fragments retain the biological activity of the HGFIN, including antigenic activity. Variants of the defined sequence and fragments also form part of the present invention. Preferred variants are those that vary from the referents by conservative amino acid substitutions.

The HGFIN proteins and polypeptides of the invention can be prepared in any suitable manner. If produced in situ, the polypeptides may be purified from appropriate sources, e.g., appropriate vertebrate cells e.g., mamilian cells for instance cells from human, mouse, bovine or rat.

Alternatively, the availability of nucleic acid molecules encoding the polypeptides enables production of the proteins using in vitro expression methods known in the art. For example, a cDNA or gene may be cloned into an appropriate in vitro transcription vector, for in vitro transcription, followed by cell-free translation in a suitable cell-free translation system. In vitro transcription and translation systems are commercially available, e.g., from Promega Biotech, Madison, Wis., or BRL, Rockville, Md. While in vitro transcription and translation is not the method of choice for preparing large quantities of the protein, it is ideal for preparing small amounts of native or mutant proteins for research purposes, particularly since it allows the incorporation of radioactive nucleotides.

According to a preferred embodiment, larger quantities of HGFIN encoded polypeptide may be produced by expression in a suitable procaryotic or eukaryotic system. For example, part or all of a DNA molecule, such as the coding portion of SEQ ID NO:1 may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA into the host cell. Such regulatory elements required for expression include promoter sequences, transcription initiation sequences and, optionally, enhancer sequences.

Secretion signals may be used to facilitate purification of the resulting protein. The coding sequence for the secretion peptide is operably linked to the 5' end of the coding sequence for the protein, and this hybrid nucleic acid molecule is inserted into a plasmid adapted to express the protein in the host cell of choice. Plasmids specifically designed to express and secrete foreign proteins are available from commercial sources. For example, if expression and secretion is desired in *E. Coli*, commonly used plasmids include pTrcPPA (Pharmacia); pPROK-C and pKK233-2 (Clontech); and pNH8a, pNH16a, pcDNAII and pAX (Stratagene), among others.

The HGFIN proteins produced by in vitro transcription and translation or by gene expression in a recombinant procaryotic or eukaryotic system may be purified according to methods known in the art. Recombinant proteins can be purified by affinity separation, such as by immunological interaction with antibodies that bind specifically to the recombinant protein or fusion proteins such as His tags, as described below. Such methods are commonly used by skilled practitioners.

As mentioned, the proteins can be produced and fused to a "tag" protein in order to facilitate subsequent purification. These fusion proteins are produced by operably-linking the nucleic acid coding sequence of the "tag" protein to the coding sequence of the protein of interest, and expressing the fused protein by standard methods. Systems are commercially available that comprise a plasmid containing an expression cassette with the "tag" protein coding sequence and a polylinker into which a coding sequence of interest can be operably ligated. These fusion protein systems further provide chromatography matrices or beads that specifically bind the "tag" protein thereby facilitating the fusion protein purification. These fusion protein systems often have the recognition sequence of a protease at or near the junction of the "tag" protein and the protein of interest so that the "tag" protein can be removed if desired. Fusion protein systems include, but are not limited to, the His-6-tag system (Quiagen) and the glutathione-S-transferase system (Pharmacia).

The HGFIN proteins of the invention, prepared by one of the aforementioned methods, may be analyzed according to standard procedures. For example, the protein may be subjected to amino acid composition, amino acid sequence, or protein concentration analysis according to known methods.

Using appropriate amino acid sequence information, synthetic HGFIN proteins of the present invention may be prepared by various synthetic methods of peptide synthesis via condensation of one or more amino acid residues, in accordance with conventional peptide synthesis methods. Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art.

The HGFIN protein can be used as a label in many in vitro applications currently used. Purified HGFIN can be covalently linked to other proteins by methods well known in the art, and used as a marker protein. The purified HGFIN protein can be covalently linked to a protein of interest in order to determine localization. In particularly preferred embodiments, a linker of 4 to 20 amino acids is used to separate HGFIN from the desired protein. This application may be used in living cells by micro-injecting the linked proteins. The HGFIN may also be linked to antibodies and used thus for localization in fixed and sectioned cells. The HGFIN may be linked to purified cellular proteins and used to identify binding proteins and nucleic acids in assays in vitro, using methods well known in the art.

The HGFIN protein can also be linked to nucleic acids and used to advantage. Applications for nucleic acid-linked HGFIN include, but are not limited, to FISH (fluorescent in situ hybridization), and labeling probes in standard methods utilizing nucleic acid hybridization.

The HGFIN proteins of the present invention can be used to identify binding partners of HGFIN. In these assays, the first protein of interest is allowed to form a physical interaction with the unknown binding protein(s), often in a heterologous solution of proteins. The complex of proteins is then isolated, and the nature of the protein complex is determined. This procedure is greatly facilitated by a simple method for isolating the HGFIN protein. For example, immunologically-specific antibodies can be used to precipitate the HGFIN protein, or the HGFIN protein can be bound to beads that can be easily purified. Such beads can be magnetized, or simply dense enough to be separated form the non-associated protein by centrifugation.

In preferred embodiments, the compositions of the invention further comprise a solid support to which the moiety detecting the HGFIN mRNA or protein is or can be attached. In certain embodiments, attachment of the detecting moiety, e.g. an antibody, nucleic acid or protein probe, is via a covalent linkage with the solid support. In other embodiments, attachment may be via a non-covalent linkage, for example, between members of a high affinity binding pair. Many examples of high affinity binding pairs are known in the art, and include biotin/avidin, ligand/receptor, and antigen/antibody pairs.

In particular aspects, the invention relates to compositions and methods for using such polypeptides and polynucleotides for treating diseases associated with increased cell proliferation, by administering a HGFIN gene or protein, in a pharmaceutically acceptable and appropriate delivery vehicle, to increase cell differentiation. Further, the compositions and methods of the present invention may be used for treating a disease associated with decreased cell proliferation by administering a HGFIN antisense sequence, in a pharmaceutically acceptable and appropriate delivery vehicle. The invention also provides immunospecific antibodies to the HGFIN protein that may be use in therapeutic compositions and methods, by themselves, or in conjugation with other therapeutic or cyto-radiotoxic agents. The compositions and methods of the present invention may also be useful in reducing the side effects of traditional chemo-radio therapies by administering a HGFIN gene, protein, or antisense sequence in conjunction with the chemo-radio therapy to thereby reduce the amount of toxic dosage needed to kill cells.

Vectors, Host Cells, and Expression

Hence, the present invention also relates to vectors that comprise a polynucleotide or polynucleotides of the present invention, and host cells that are genetically engineered with vectors of the invention and to the production of polypeptides of the invention by recombinant techniques both in vitro and in vivo, as well as ex vivo procedures. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. In accordance with the methods of the present invention, host cells may also be obtained from the BM of a subject by procedures well known in the medical arts. Introduction of polynucleotides into host cells can then be effected by methods described in many standard laboratory manuals, such as Davis et al., *Basic Methods In Molecular Biology* (1986) and Sambrook et al., *Molecular Cloning: A Laboratory Manual, 2nd Ed.*, Cold Spring Harbor Laboratory Press, Cold Spring Harbor, N.Y. (1989) such as calcium phosphate transfection, DEAE-dextran mediated transfection, microinjection, cationic lipid-mediated transfection, electroporation, transduction, scrape loading, ballistic introduction or infection.

Representative examples of appropriate hosts for in vitro procedures include bacterial cells, such as streptococci, staphylococci, *E. coli, Streptomyces* and *Bacillus subtilis* cells; fungal cells, such as yeast cells and Aspergiffits cells, insect cells such as *Drosophila* S2 and *Spodoptera* Sf9 cells; animal cells such as CHO, COS, HeLa, C127, 3T3, BHK, HEK 293 and Bowes melanoma cells, and plant cells. The selection of an appropriate host is deemed to be within the scope of those skilled in the art from the teachings herein.

More particularly, the present invention also includes recombinant constructs comprising a HGFIN DNA, cDNA or RNA sequence as well as compliment nucleotide sequences for triplexing duplex DNA. The construct comprises a vector, such as a plasmid or viral vector, into which the clone has been inserted, in a forward or reverse orientation. In a preferred aspect of this embodiment, the construct further comprises regulatory sequences, including, for example, a promoter, operably linked to the genetic sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX 174, pbluescriot SK, pbsks, pNH8A, pNH 16a, pNHI8A, pNH46A (Stratagene); ptrc99a, pKK223-3, pKK233-3, pDR540, pRIT5 (Pharmacia); Eukaryotic: pWLNEO, pSV2CAT, pOG44, pXTI, pSG (Stratagene) pSVK3, pBPV, pMSG, pSVL (Pharmacia). As further examples, cDNA of human HGFIN may be inserted in the pEF/myc/cyto vector (from Invitrogen) and/or the pCMV-Tag3b vector (from Stratagene), which can then be used with anti-Myc Ab, to transform Stem or Hela (or other) cells with the HGFIN DNA. The protein HGFIN produced may be purified from the cells and directly injected to the BM tissue, infused to blood cells, or delivered in a lyophilized carrier as described above.

However, any other plasmid or vector may be used as long as they are replicable and viable in the host. In addition, a complete mammalian transcription unit and a selectable marker can be inserted into a prokaryotic plasmid for use in in vivo procedures. The resulting vector is then amplified in bacteria before being transfected into cultured mammalian cells or delivered directly to the subject with an acceptable biological carrier as described below. Examples of vectors of this type include pTK2, pHyg and pRSVneo. Hence, these plasmids, constructs and vectors may be used in both in vivo and ex vivo procedures. Ex vivo procedures involve the removal of a host cell, such as a BM, stromal or stem cell, from the subject, recombinant manipulation of the cell (i.e., transformation, transduction or transfection with a suitable HGFIN expression system vector), and the re-delivery of the cell back into its host environment.

Further, according to one particular embodiment of the present invention, recombinant HGFIN DNA, cDNA, RNA, or polynucleotide sequence coding for the antisense sequence encoding the protein, may be directly injected to the BM for the production or inhibition of HGFIN endogenously. DNA, cDNA, RNA or polynucleotide sequences coding for the antisense sequence encoding the protein may also be delivered using other appropriate means, including vectors, as described below, and well known in the recombinant arts.

A wide variety of recombinant plasmids may be engineered to express the HGFIN protein and used to delivery HGFIN to a cell. These include the use of naked DNA and HGFIN plasmids to directly transfer genetic material into a cell (Wolfe et al., 1990); formulations of HGFIN encoding trapped liposomes (Ledley et. al., 1987) or in proteoliposomes that contain other viral envelope receptor proteins (Nicolau et al., 1983); and HGFIN-encoding DNA, or antisense sequence, coupled to a polysineglycoprotein carrier complex. Hence methods for the delivery of nucleotide sequences to cells are well known in the recombinant arts. Such methods for in vitro delivery, further include, but are not limited to: microinjection, calcium phosphatase, lyposomes, and electroporation.

Genetic material, such as the nucleotides of the present invention, may be delivered to cells, in vivo, using various different plasmid based delivery platforms, including but not limited to recombinant ADV (such as that described in U.S. Pat. No. 6,069,134 incorporated by reference herein), AAV (such as those described by U.S. Pat. No. 5,139,941 incorporated by reference herein), MMLV, Herpes Simplex Virus (U.S. Pat. No. 5,288,641, incorporated by reference herein), cytomegalovirus, lentiviral, and overall, retroviral gene delivery systems, well known and practiced with in the art.

Techniques for preparing replication defective, infective viruses are well known in the art, as exemplified by Ghosh-Choudhury & Graham (9187); McGory et al. (1988); and Gluzman et al. (1982), each incorporated by reference herein. These systems typically include a plasmid vector including a promoter sequence (such as CMV early promoter) operably linked to the nucleotide coding the gene of interest (inserted into an appropriate gene insertion site; i.e., an IRES site), as well as a terminating signal (such as a Poly-A tail i.e., BGH), and the appropriate mutations so as to make the delivery vehicle replication defective (e.g., Psi sequence deletions) and safe for therapeutic uses. The construction of the appropriate elements in a vector system containing the nucleotides of the present invention is well within the skills of one versed in the recombinant arts.

A great variety of vector and/or expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia, viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *Molecular Cloning, A Laboratory Manual* (supra).

Promoter regions can be selected from any desired gene using CAT (chloramphenicol acetyl transferase) vectors or other vectors with selectable markers. Two appropriate vectors are pKK232-8 and pCM7. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art.

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HGFIN polypeptide is to be expressed for use in screening assays, generally, it is preferred that the polypeptide be produced at the surface of the cell. In this event, the cells may be harvested prior to use in the screening assay. If the HGFIN polypeptide is secreted into the medium, the medium can be recovered in order to recover and purify the polypeptide; if produced intracellularly, the cells must first be lysed before the polypeptide is recovered. The HGFIN polypeptides can be recovered and purified from recombinant cell cultures by well known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Further still, the recombinant HGFIN DNA, cDNA, RNA or polynucleotide sequences coding for the antisense sequence encoding the protein, may be delivered to the cells of the BM for the production or inhibition of HGFIN endogenously, by use of biologically compatible carriers or excipients. This may be useful in inducing or inhibiting cell differentiation and/or possibly proliferation. Pharmaceutically acceptable carriers for therapeutic use are well known in the pharmaceutical art, and are described, for example, in Remington's Pharmaceutical Sciences (A. P. Gennaro, ed.; Mack, 1985). For example, sterile saline or phosphate-buffered saline at physiological pH may be used. Preservatives, stabilizers, dyes, and even flavoring agents may be provided in the pharmaceutical composition. For example, sodium benzoate, sorbic acid, and esters of p-hydroxybenzoic acid may be added as preservatives. Antioxidants and suspending agents may also be used.

The above-described constructs, plasmids and vectors are useful in gene therapy procedures. Successful gene therapy generally requires the integration of a gene able to correct the genetic disorder into the host genome, where it would co-exist and replicate with the host DNA and be expressed at a level to compensate for the defective gene. Ideally, the disease would be cured by one or a few treatments, with no serious side effects. There are several approaches to gene therapy proposed.

As described above, basic transfection methods exist in which DNA containing the gene of interest is introduced into cells non-biologically, for example, by permeabilizing the cell membrane physically or chemically. Liposomes or protein conjugates formed with certain lipids and amphophilic peptides can be used for transfection. (Stewart et al., 1992; Torchilin et al., 1992; Zhu et al., 1993, incorporated herein by reference.) This approach is particularly effective in ex vivo procedures involving leukocytes, which can be temporarily removed from the body and can tolerate the cytotoxicity of the treatment.

A second, transduction approach, capitalizes on the natural ability of viruses to enter cells, bringing their own genetic material with them. For example, Retroviruses have promise as gene delivery vectors due to their ability to integrate their genes into the host genome, transferring a large amount of foreign genetic material, infecting a broad spectrum of species and cell types and of being packaged in special cell-lines (Miller, 1992, incorporated herein by reference).

A third method uses other viruses, such as adenovirus, herpes simplex virues (HSV), cytomegalovirus (CMV), and adeno-associated virus (AAV), which are engineered to serve as vectors for gene transfer. Although some viruses that can accept foreign genetic material are limited in the number of nucleotides they can accommodate and in the range of cells they infect, these viruses have been demonstrated to successfully effect gene expression. For example, adenovirus gene transfer systems may be used. Such a system is based upon recombinant, engineered adenovirus which is rendered replication-incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 Kb of foreign DNA and can be grown to high titers in 293 cells (Stratford-Perricaudet and Perricaudet, 1991a). Surprisingly persistent expression of transgenes following adenoviral infection has also been reported.

The pharmaceutical compositions of the present invention may be formulated and used as tablets, capsules, or elixirs for oral administration; suppositories for rectal or vaginal administration; sterile solutions and suspensions for parenteral administration; creams, lotions, or gels for topical administration; aerosols or insufflations for intratracheobronchial administration; and the like. Preparations of such formulations are well known to those skilled in the pharmaceutical arts. The dosage and method of administration can be tailored to achieve optimal efficacy and will depend on factors that those skilled in the medical arts will recognize.

When administration is to be parenteral, such as intravenous on a daily basis, injectable pharmaceuticals may be prepared in conventional forms, either as liquid solutions or suspensions; solid forms suitable for solution or suspension in liquid prior to injection; or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g. liposomes) may be utilized.

Hence, in another preferred embodiment the present invention is directed to a novel pharmaceutical composition that includes a biologically acceptable carrier along with an effective amount of a HGFIN DNA, cDNA, RNA or protein for the treatment and/or prevention of diseases associated with a lack of progenitor cell differentiation. The pharmaceutical composition includes a HGFIN sequence substantially identical to SEQ. ID. No. 1 and/or a protein encoded by an amino acid sequence substantially identical to the sequence of SEQ. ID. 2. For the treatment of and/or prevention of diseases associated with an unhealthy increase in progenitor cell differentiation, a pharmaceutical composition that includes an effective amount of a nucleotide sequence coding for the antisense sequence of SEQ. ID. 1, may be administered. An example of such diseased state that may be treated by the compositions of the present invention are leukemia and lymphoma.

Hence, methods for the treatment of diseases associated with an unhealthy increase or lack of stem or progenitor cell differentiation in a subject are also provided. These methods involve administering to the subject a pharmaceutical composition that includes an effective amount of a HGFIN protein or a nucleotide sequence coding for the HGFIN protein or a nucleotide sequence that codes for the anti-sense sequence of the nucleotide sequence coding for the HGFIN protein. These may be delivered by suitable means, as described above, including the use of vectors and or acceptable biological carriers. The above disclosed vectors may be targeted preferentially to different forms of lymphoproliferative diseases by use of antibodies that recognize specific epitopes on the cell surface of these abnormal cells. The production and use of such antibodies are well known in the recombinant arts but include, for example anti-CD20, for B-cell lymphoma; anti-CD52 for Chronic Lymphocytic Leukemia; Anti-CD33 linked to a chemotherapeutic agent (calicheamicin), for Acute Myeloid Leukemia; and an IL-2 gene linked to diphtheria toxin, for T-cell lymphoma.

Antibodies

The present invention also provides antibodies capable of immunospecifically binding to polypeptides of the invention. Polyclonal or monoclonal antibodies directed towards the polypeptide encoded by HGFIN may be prepared according to standard methods. Monoclonal antibodies may be prepared according to general hybridoma methods of Kohler and Milstein, *Nature* (1975) 256:495–497), the trioma technique, the human B-cell hybridoma technique (Kozbor et al., *Immunology Today* (1983) 4:72) and the EBV-hybridoma technique (Cole et al, *Monoclonal Antibodies And Cancer Therapy*, pp. 77–96, Alan R. Liss, Inc., 1985).

Antibodies utilized in the present invention may be polyclonal antibodies, although monoclonal antibodies are preferred because they may be reproduced by cell culture or recombinantly, and may be modified to reduce their antigenicity. Polyclonal antibodies may be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, a HGFIN antigen comprising an antigenic portion of the HGFIN polypeptide is initially injected into any of a wide variety of mammals (e.g., mice, rats, rabbits, sheep or goats). Alternatively, in order to generate antibodies to relatively short peptide portions HGFIN, a superior immune response may be elicited if the polypeptide is joined to a carrier protein, such as ovalbumin, BSA or KLH. The peptide-conjugate is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

Preferably, the immortal fusion partners utilized are derived from a line that does not secrete immunoglobulin. The resulting fused cells, or hybridomas, are cultured under conditions that allow for the survival of fused, but not unfused, cells and the resulting colonies screened for the production of the desired monoclonal antibodies. Colonies producing such antibodies are cloned, expanded, and grown so as to produce large quantities of antibody, see Kohler and Milstein, 1975 Nature 256:495 (the disclosures of which are hereby incorporated by reference).

Large quantities of monoclonal antibodies from the secreting hybridomas may then be produced by injecting the clones into the peritoneal cavity of mice and harvesting the ascites fluid therefrom. The mice, preferably primed with pristine, or some other tumor-promoter, and immunosuppressed chemically or by irradiation, may be any of various suitable strains known to those in the art. The ascites fluid is harvested from the mice and the monoclonal antibody purified therefrom, for example, by CM Sepharose column or other chromatographic means. Alternatively, the hybridomas may be cultured in vitro or as suspension cultures. Batch, continuous culture, or other suitable culture processes may be utilized. Monoclonal antibodies are then recovered from the culture medium or supernatant.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell.). When antibody gene synthesis is induced in the transfected host, the heavy and light chain proteins self-assemble to produce active antibodies that can be detected by screening with the antigen or immunogen.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference.) Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In a preferred embodiment, antibodies are prepared, which react immunospecifically with various epitopes of the HGFIN encoded polypeptides. These above-described antibodies may be employed to isolate or to identify clones expressing the polypeptide or to purify the polypeptides by affinity chromatography. Further, these antibodies may be used for therapeutic purposes by binding to the endogenous HGFIN receptor and thereby impeding the binding of the natural ligand, where it is desirable to inhibit leukocyte proliferation. Specific antibodies may be made in vivo using recombinant DNA and methods well know in the art.

Antibodies that are immunologically specific to HGFIN proteins, or specific epitopes thereof, may be utilized in affinity chromatography to isolate the HGFIN protein, to quantify the protein utilizing techniques such as western blotting and ELISA, or to immuno-precipitate HGFIN from a sample containing a mixture of proteins and other biological materials. The immuno-precipitation of HGFIN is particularly advantageous when utilized to isolate binding partners of HGFIN, as described above. Antibodies against HGFIN polypeptides may also be employed to treat diseases associated with an increased rate of differentiation of progenitor cells, namely, the various lymphoproliferative diseases detailed above, among other hematopoietic pathological conditions.

As described above, the HGFIN antibodies for use in the present invention may have utility on their own without conjugation, if they alter the native activity of HGFIN in the aberrant cells. Such antibodies, which may be selected as described above, may be utilized without further modification to include a cytotoxic moiety. These types of compositions have the advantage of reduced toxicity (in that only the toxicity of the antibody moieties themselves must be taken into account when dosing), and are simpler to manufacture: thus, non-conjugated activity altering anti-HGFIN antibody therapeutics are a preferred embodiment of the invention. However, the conjugation of cytotoxic agents is yet another preferred embodiment when utilizing these antibodies, as the added moieties also add functionality to the therapeutic. Further, the antibodies of the present invention can be used as a delivery vehicle to target the delivery of other various elements (i.e., a genetic sequence encoding a HGFIN polynucleotide or its antisense sequence) to HGFIN expressing cells.

In certain preferred embodiments of the invention, the anti-HGFIN antibodies may be coupled or conjugated to one or more therapeutic or cytotoxic moieties. As used herein, "cytotoxic moiety" simply means a moiety that inhibits cell growth or promotes cell death when proximate to or absorbed by the cell. Suitable cytotoxic moieties in this regard include radioactive isotopes (radionuclides), chemotoxic agents such as differentiation inducers, inhibitors and small chemotoxic drugs, toxin proteins and derivatives thereof, as well as the nucleotide sequences (or their antisense sequence) of the present invention.

In general, therapeutic agents may be conjugated to the antiHGFIN moiety by any suitable technique, with appropriate consideration of the need for pharmokinetic stability and reduced overall toxicity to the patient. A therapeutic agent may be coupled to a suitable antibody moiety either directly or indirectly (e.g. via a linker group). A direct reaction between an agent and an antibody is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer to distance an antibody from an agent in order to avoid interference with binding capabilities. A linker group can also serve to increase the chemical reactivity of a substituent on a moiety or an antibody, and thus increase the coupling efficiency. An increase in chemical reactivity may also facilitate the use of moieties, or functional groups on moieties, which otherwise would not be possible.

Suitable linkage chemistries include maleimidyl linkers and alkyl halide linkers (which react with a sulfhydryl on the antibody moiety) and succinimidyl linkers (which react with a primary amine on the antibody moiety). Several primary amine and sulfhydryl groups are present on immunoglobulins, and additional groups may be designed into recombinant immunoglobulin molecules. It will be evident to those skilled in the art that a variety of bifunctional or polyfunctional reagents, both homo- and heterofunctional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology, e.g., U.S. Pat. No. 4,671,958.

As an alternative coupling method, cytotoxic agents may be coupled to the anti-HGFIN antibody moiety through a an oxidized carbohydrate group at a glycosylation site, as described in U.S. Pat. Nos. 5,057,313 and 5,156,840. Yet another alternative method of coupling the antibody moiety to the cytotoxic or imaging moiety is by the use of a non-covalent binding pair, such as streptavidin/biotin, or avidin/biotin. In these embodiments, one member of the pair is covalently coupled to the antibody moiety and the other member of the binding pair is covalently coupled to the cytotoxic or imaging moiety.

Where a cytotoxic moiety is more potent when free from the antibody portion of the immunoconjugates of the present invention, it may be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

It may be desirable to couple more than one therapeutic, cytotoxic and/or imaging moiety to an antibody. By polyderivatizing the anti-HGFIN antibody, several cytotoxic strategies may be simultaneously implemented, an antibody may be made useful as a contrasting agent for several visualization techniques, or a therapeutic antibody may be labeled for tracking by a visualization technique. In one embodiment, multiple molecules of a cytotoxic moiety are coupled to one antibody molecule. In another embodiment, more than one type of moiety may be coupled to one antibody. For instance, a therapeutic moiety, such as an HGFIN polynucleotide or antisense sequence, may be conjugated to an antibody in conjunction with a chemo- or radiotoxic moiety, to increase the effectiveness of the chemo- or radiotoxic therapy, as well as lowering the required dosage necessary to obtain the desired therapeutic effect. Regardless of the particular embodiment, immunoconjugates with more than one moiety may be prepared in a variety of ways. For example, more than one moiety may be coupled directly to an antibody molecule, or linkers that provide multiple sites for attachment (e.g., dendrimers) can be used. Alternatively, a carrier with the capacity to hold more than one cytotoxic moiety can be used.

As explained above, a carrier may bear the agents in a variety of ways, including covalent bonding either directly or via a linker group, and non-covalent associations. Suitable covalent-bond carriers include proteins such as albumins (e.g., U.S. Pat. No. 4,507,234), peptides, and polysaccharides such as aminodextran (e.g., U.S. Pat. No. 4,699,784), each of which have multiple sites for the attachment of moieties. A carrier may also bear an agent by non-covalent associations, such as non-covalent bonding or by encapsulation, such as within a liposome vesicle (e.g., U.S. Pat. Nos. 4,429,008 and 4,873,088). Encapsulation carriers are especially useful in chemotoxic therapeutic embodiments, as they can allow the therapeutic compositions to gradually release a chemotoxic moiety over time while concentrating it in the vicinity of the target cells.

Preferred radionuclides for use as cytotoxic moieties are radionulcides which are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use. $^{131}$I, is particularly preferred, as are other β-radiation emitting nuclides, which have an effective range of several millimeters. $^{123}$I, $^{125}$I, $^{131}$I, or $^{211}$At may be conjugated to antibody moieties for use in the compositions and methods utilizing any of several known conjugation reagents, including Iodogen, N-succinimidyl 3-[$^{211}$At]astatobenzoate, N-succinimidyl 3-[$^{131}$I]iodobenzoate (SIB), and, N-succinimidyl 5-[$^{131}$I]iodob-3-pyridinecarboxylate (SIPC). Any iodine isotope may be utilized in the recited iodo-reagents. Other radionuclides may be conjugated to anti-HGFIN antibody moieties by suitable chelation agents known to those of skill in the nuclear medicine arts.

Preferred chemotoxic agents include small-molecule drugs such as methotrexate, and pyrimidine and purine analogs. Preferred chemotoxin differentiation inducers include phorbol esters and butyric acid. Chemotoxic moieties may be directly conjugated to the anti-HGFIN antibody moiety via a chemical linker, or may encapsulated in a carrier, which is in turn coupled to the anti-HGFIN antibody moiety.

Preferred toxin proteins for use as cytotoxic moieties include ricin, abrin, diphtheria toxin, cholera toxin, gelonin, *Pseudomonas* exotoxin, *Shigella* toxin, pokeweed antiviral protein, and other toxin proteins known in the medicinal biochemistry arts. As these toxin agents may elicit undesirable immune responses in the patient, especially if injected intravascularly, it is preferred that they be encapsulated in a carrier for coupling to the anti-HGFIN antibody moiety.

Delivery/Administration of Therapeutic Antibodies:

For administration, the antibody-therapeutic agent will generally be mixed, prior to administration, with a non-toxic, pharmaceutically acceptable carrier substance. Usually, this will be an aqueous solution, such as normal saline or phosphate-buffered saline (PBS), Ringer's solution, lactate-Ringer's solution, or any isotonic physiologically acceptable solution for administration by the chosen means. Preferably, the solution is sterile and pyrogen-free, and is manufactured and packaged under current Good Manufacturing Processes (GMP's), as approved by the FDA. The clinician of ordinary skill is familiar with appropriate ranges for pH, tonicity, and additives or preservatives when formulating pharmaceutical compositions for administration by intravascular injection, intrathecal injection, injection into the BM, direct injection into the aberrant cell, or by other routes. In addition to additives for adjusting pH or tonicity, the antibody-therapeutics agent may be stabilized against aggregation and polymerization with amino acids and non-ionic detergents, polysorbate, and polyethylene glycol.

Optionally, additional stabilizers may include various physiologically-acceptable carbohydrates and salts. Also, polyvinylpyrrolidone may be added in addition to the amino acid. Suitable therapeutic immunoglobulin solutions, which are stabilized for storage and administration to humans, are described in U.S. Pat. No. 5,945,098, incorporated fully herein by reference. Other agents, such as human serum albumin (HSA), may be added to the therapeutic composition to stabilize the antibody conjugates. The compositions of the invention may be administered using any medically appropriate procedure, e.g., intravascular (intravenous, intraarterial, intracapillary) administration, injection into the BM, intracavity or direct injection in the aberrant cell. Intravascular injection may be by intravenous or intraarterial injection.

The effective amount of the therapeutic antibody-conjugate composition to be given to a particular patient will depend on a variety of factors, several of which will be different from patient to patient. A competent clinician will be able to determine an effective amount of a therapeutic antibody-conjugate composition to administer to a patient to retard the growth and promote the death of leukemia/lymphoma associated cells. Dosage of the antibody-conjugate will depend on the treatment of the tumor, route of administration, the nature of the therapeutics, sensitivity of the tumor to the therapeutics, etc. Utilizing $LD_{50}$ animal data, and other information available for the conjugated cytotoxic or imaging moiety, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions, which are rapidly cleared from the body, may be administered at higher doses, or in repeated doses, in order to maintain a therapeutic concentration. Utilizing ordinary skill, the competent clinician will be able to optimize the dosage of a particular therapeutic composition in the course of routine clinical trials.

Typically the dosage will be 0.001 to 100 milligrams of conjugate per Kilogram subject body weight. Doses in the range of 0.01 to 1 mg per kilogram of patient body weight may be utilized for a radionuclide therapeutic composition that is administered intrathecally. In a therapeutic example, where the therapeutic composition comprises a $^{131}I$ cytotoxic moiety, the dosage to the patient will typically start at a lower range of 10 mCi, and go up to 100, 300 or even 500 mCi. Stated otherwise, where the therapeutic agent is $^{131}I$, the dosage to the patient will typically be from 5,000 Rads to 100,000 Rads (preferably at least 13,000 Rads, or even at least 50,000 Rads). Doses for other radionuclides are typically selected so that the tumoricidal dose will be equivalent to the foregoing range for $^{131}I$. Similarly, chemotoxic or toxin protein doses may be scaled accordingly.

The antibody conjugate can be administered to the subject in a series of more than one administration. For therapeutic compositions, regular periodic administration (e.g., every 2–3 days) will sometimes be required, or may be desirable to reduce toxicity. For therapeutic compositions that will be utilized in repeated-dose regimens, antibody moieties that do not provoke HAMA or other immune responses are preferred.

The foregoing is intended to be illustrative of the embodiments of the present invention, and are not intended to limit the invention in any way. Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein. All publications and patent applications are herein incorporated by reference to the same extent as if each individual publication or patent application was specifically and individually indicated to be incorporated by reference.

EXAMPLES

The following description sets forth the general procedures involved in practicing the present invention. To the extent that specific materials are mentioned, it is merely for purposes of illustration and is not intended to limit the invention.

All ligands for the putative HGFIN transmembrane protein are unknown. Since the HGFIN clone was retrieved through screening of cDNA libraries with an NK-1-specific probe, it is believed that the natural ligand for NK-1 is likely responsible for interacting with HGFIN. The 3-D structures of the PKD region from HGFIN (FIG. 3A) was used to determine interactions with SP, which is the preferred ligand for NK-1 (FIG. 3C). Based on the putative spatial arrangement of the HGFIN protein (FIG. 2), SP could contact the extracellular PKD region, after all, the electrostatic differences between SP (17) and PKD could explain the formation of a possible complex (FIG. 3Q). See the examples below for further details.

Unless other-wise specified, general cloning procedures, such as those set forth in Sambrook et al, *Molecular Cloning*, supra or Ausubel et al. (eds) *Current Protocols in Molecular Biology*, John Wiley & Sons (2000) (hereinafter "Ausubel et al.") are used.

Example I

A. Reagents

Hoffman-La Roche (Nutley, N.J.) provided recombinant human (rh) IL-1α. Stem cell factor (rhSCF), rhIL-6, rhIL-11 and alkaline phosphatase (Alk Phos)-conjugated goat anti-rabbit IgG were purchased from R&D Systems (Minneapolis, Minn.). IL-1β and nerve growth factor (NGF) were purchased from Collaborative Research (Bedford, Mass.) and Amersham Life Science (Cleveland, Ohio) respectively. The following was purchased from Sigma (St Louis, Mo.): Isopropyl-D-Thioglactopyranoside (IPTG), SP, Ficoll Hypaque, lipopolysaccharide (LPS), Fibronectin-Fragment III-C (FN-IIIC), 12-0-tetradecanoylphorbol diester (TPA), dimethylsulfoxide (DMSO) and cytochemical staining kits for 2-naphthyl-acetate esterase and naphthol AS-D chloroacetate esterase. SP was dissolved in sterile distilled water and then immediately solublized with nitrogen gas. The reconstituted SP was used within two days. The immunology department of Genetics Institute (Cambridge, Mass.) provided the human G-CSF and M-CSF. Rabbit anti-Id2 was purchased from Santa Cruz Biotechnology (Santa Cruz, Calif.). Rabbit anti-Histidine Affinity Tag (HAT) and HAT-affinity resin were purchased from Clonetech (Palo Alto, Calif.). The HAT protein expression system (pHAT10) was also purchased from Clonetech.

B. Cell Lines

With regard to primary human cell lines, BM aspirates and peripheral blood from healthy human volunteers between the ages of 25 to 35 years, were used. Samples were obtained following informed consent. The institutional review board of UMDNJ-New Jersey Medical School, Newark, N.J., approved the use of human tissues. The BM aspirates were used to prepare stromal cultures and to isolate BMNC. The peripheral blood was used to isolate mononuclear cells (PMNC). BMNC and PBMC were isolated by Ficoll-Hypaque density gradient.

Breast cancer cell lines (DU4475 and T-47D), human melanoma cell line (SK-Mel) and normal mammary epithelial cell line (MCF-12A) were purchased from American Type Culture Collection, ATCC (Manassas, Va.). Cells were cultured as per ATCC instructions. HL-60 cells were obtained from Dr. George Studzinski, UMDNJ-New Jersey Medical School, Department of Laboratory Medicine and Pathology. HL-60 were cultured in RPMI 1640 (Sigma) containing 10% fetal calf serum, FCS (Hyclone Laboratories, Logan, Utah).

C. Bone Marrow Stromal Culture

Stromal cultures were prepared from BM aspirates of healthy donors, ages 20 to 35 years. Use of human tissue followed the guidelines of the institutional review board, UMDNJ-New Jersey Medical School. Cultures were prepared as described (16). Briefly, unfractionated cells from BM aspirates were cultured at 33° C. and after day 3, RBC and granulocytes were removed by Ficoll-Hypaque density gradient. Cultures were maintained with weekly replacement of 50% medium until confluence.

D. cDNA Libraries

Three different cDNA libraries were screened with an NK-1 probe (11). One cDNA library, constructed from unstimulated pooled human BM cells was purchased from Clontech (Palo Alto, Calif.). Two of the cDNA libraries were prepared with mRNA from IL-1α or SCF cytokine-stimulated BM stroma as described (17). Briefly, BM stroma from more than 9 healthy donors were stimulated with 25 ng/ml IL-1α or 10 ng/ml SCF and the pooled mRNA used to construct the cDNA library. BM donors were selected based on sex and ethnic diversity. Libraries were constructed using the ZAP Express cDNA Gigapack III Gold cloning kit (Stratagene, La Jolla, Calif.). Xho I and EcoR I adapters were ligated in pZAP, which resulted in $\sim 10^6$–$10^7$ pfu/ml. Each library was screened with $10^7$ pfu at $5 \times 10^4$ pfu/150 mm agar. Plaques were hybridized with a 0.65 kb fragment of NK-1 cDNA (11) using different hybridization and washing parameters. The insert from seven phagemid was amplified using T3/T7 primers and the PCR products were ligated into pCR2.1 (Invitrogen, Carlsbad, Calif.). The inserts were sequenced in the Molecular Core Facility of UMDNJ-New Jersey Medical School. The first set of DNA sequence was performed with the M13 forward and reverse primers, followed by five other sequencing with overlapping primers. Alignment of the overlapping DNA fragments indicated that the insert was equivalent to 2662 bp.

Example 2

A. Cell Differentiation

Cell differentiation was performed with a myelomonocytic cell line, HL-60, or BM mononuclear cells (BMNC). HL-60 cells were chemically differentiated with TPA and DMSO for monocytes and granulocytes respectively (18, 19). BMNC were isolated from BM aspirate of healthy donors using Ficoll Hypaque density gradient. The IRB of UMDNJ-Newark Campus approved the use of human BM aspirate for these studies.

Further, BMNC cells were differentiated with M-CSF or G-CSF (500 U/ml for each) to monocytes and granulocytes respectively. Undifferentiated cells were cultured in parallel with only media. Culture media were replaced at two-day intervals until cytochemical staining determined that >90% of the cells were differentiated. At this time, cell differentiation was terminated and the cells analyzed by northern analyses for Id2 and HGFIN mRNA, and by immunoblot for Id2 protein. For HL-60 cultures, cytochemical staining was performed after three days with 100–200 cells. Beginning at day 5, cells from cultures with BMNC were stained and daily thereafter. Neutrophil and monocyte staining were performed with kits specific for 2-naphthyl-acetate esterase and naphthol AS-D chloroacetate esterase respectively.

B. Cell Stimulation

Peripheral blood mononuclear cells (PBMC) were resuspended in RPMI 1640 containing 2% FCS at $10^6$/Ml. Cell suspension, 10 ml, was stimulated with 1 μg/ml of LPS. BM stroma was stimulated in sera-free α-MEM (Sigma) with the following: 10 ng/ml SCF, 5 ng/ml IL-11, 5 U/ml IL-1α, 5 ng/ml IL-1α, 25 ng/ml NGF and 10 ng/ml IL-6. Dose-response curves with slot blots for HGFIN mRNA determined the optimal concentration of each stimulus. During stromal cell stimulation, culture media were supplemented with insulin-transferring-selenium-A (Life Technologies, Grand Island, N.Y.). In both types of cells, controls included parallel cultures in similar media. At 8 and 16 h, total RNA was extracted from each experimental point and control and then analyzed by northern analyses for HGFIN mRNA.

C. Northern Analysis

Northern analysis for steady state HGFIN mRNA was performed as described (20). Total RNA was extracted from the experimental cells and 10 μg from each was separated in 1.2% agarose. RNA was transferred to nylon membranes (S & S Nytran, Keene, N.H.) and then hybridized with [α-$^{32}$P]-dATP-labeled cDNA probes specific for HGFIN or Id2. Membranes were stripped and then reprobed with cDNA for 18S rRNA. Probes were randomly labeled with [α-$^{32}$P]-dATP, 3,000 Ci/mM, (Dupont/NEN, Boston, Mass.) using the Prime-IT II random primer kit (Stratagene). The membrane was placed in a phosphoimager cassette (Molecular Dynamics, Sunnyvale, Calif.) and then scanned at different times beginning at 6 h to 24 h on a Phospholmager (Molecular Dynamics). Negative results were not attributed to the lack of total RNA on the membrane since each was hybridized with a cDNA probe for 18S rRNA.

D. cDNA Probes

Transformed bacteria containing cDNA inserts for 18S rRNA and β-actin were purchased from ATCC. Id2 and HGFIN inserts were ligated in pCR 2.1 (described below). Each of the cDNA probe used in this study was excised with EcoRI. The human Id2 cDNA was cloned by RT-PCR using 2 μg of total RNA obtained from differentiated HL-60 cells. Primers specific for Id2 were designed from the reported sequence (15) and synthesized at the Molecular Core Facility of UMDNJ-New Jersey Medical School: 5'-CCG GTG CCA AGC GCA CCT-3' (sense, +208/+225) and 5'-CGC TTA TTC AGC CAC ACA.G-3'(antisense, +762/+780). The following profile was used to amplify the Id2 fragment using 35 cycles: 95° C. for 30 sec, annealing at 60° C. for 30 sec, and extension at 72° C. for 1 min. The sample was subjected to a final extension at 72° C. for 7 min. The PCR reactions containing the predicted fragments (508 bp) were purified using QlAquick Gel Extraction Kit (Valecia, Calif.). The purified DNA was subcloned into pCR 2.1 and then sequenced at the Molecular Core Facility at UMDNJ using the M13 forward and reverse primers. Analyses of the sequence indicated that the selected fragment was >99% similar to the published clone for Id2 (15).

E. Western Blots

Differentiated and undifferentiated BMNC were washed and resuspended in PBS, pH 7.4 containing 1 mM PMSF and 5 μM leupeptin (both protease inhibitors purchased from Sigma). Cell extracts were prepared by subjecting the cells to three cycles of freeze-thaw using an ethanol/dry ice bath and a 37° C. water bath. Extracts were centrifuged at 10,000 g for 10 min and then determined for total protein concentration using the BioRad Protein Assay kit (BioRad Laboratories, Herrcules, Calif.). Extracts (15 Vig) were analyzed by western blot for Id2 protein as described (26). Briefly, proteins were separated on a gradient SDS-PAGE ranging from 10–20%. Proteins were transblotted to PVDF transfer membrane (NEN Life Sciences, Boston, Mass.) for 1 h at 60 volts. Membranes were incubated with anti-Id2 (1/2000) at room temperature overnight followed by incubation with Alk Phos-conjugated anti-rabbit IgG for 2 h at room temperature. Alk Phos activity was detected with BCIP/NBT substrate System (Kirkeguard & Perry Laboratories, Gaithersburg, Md.). The M, of the developed bands were compared with Rainbow colored markers (Amersham Life Science, Arlington Heights, Ill.).

Example 3

A. Purification of HGFIN from a Prokaryotic Expression Vector

PCR was used to amplify the coding region of HGFIN, +60/+1760 (FIG. 1, Genbank accession number AF322909). The following primer pairs were used in the PCR reaction: 5'cgg ggtacc atggaatgtctctacta 3' (SEQ ID NO:3) (upstream with Kpn I linker) and 5' ccg gaattc tcgaaatttaagaaact 3' (SEQ ID NO:4) (downstream with EcoR I linker). The HGFIN-specific sequences are underlined for both the upstream and downstream primers.

The amplified DNA fragment was cloned into pHAT10, hereafter referred as pHAT10-HGFIN. The vector was transformed into bacteria and HGFIN-HAT induced with IPTG. Induced bacterial cultures (20 ml) were sonicated in 2 ml of 100 mM Tris, pH 6.8/4% SDS. After this, HGFIN was verified in the cell-free lysates by western blots using 15 μg of total protein and rabbit anti-HAT. Details on the technique for western blot are described above. The lysates that showed a band at the predicted size of ~66 kDa were further purified with the HAT-affinity resin (TALON Metal Affinity Resins, Clontech). The purification procedure followed manufacturer's protocol. Bacterial cultures, 20 ml, provided ~0.5 mg of total HGFIN protein. The purified proteins from different purification procedures were pooled and then verified by purified HGFIN by western blots.

B. ProteinChip Analyses for HGFIN-SP Interaction

Before studying the interaction between SP and HGFIN, each protein was profiled by the Surface Enhanced Laser Desorption/Ionization (SELDI) ProteinChip Array technology (Ciphergen Biosystems Inc., Fremont, Calif.). Normal phase (NP1) arrays were used for profiling and preactivated surface arrays (PS1) for HGFIN-SP interaction. For profiling studies, 2 μg of purified HGFIN or 2 μg of SP were spotted directly onto the NP1 arrays. Prior to adding of the proteins, chips were pre-wet with PBS. Arrays were incubated at room temperature until the protein was absorbed, which as approximately 5 to 10 min. After this, 0.5 μl of sinapinic acid (SPA) (Ciphergen Biosystems), diluted at 1:50 in 50% acetonitrile and 0.5% trifluoroacetic acid was added to the arrays. Chips were immediately analyzed using linear, time-lag focusing laser desorption/ionization SELDI-time-of-flight mass spectrometer (Model PBS II). Accurate mass was determined by collecting approximately 150 averaged laser shots. The range of molecular mass that was used to calibrate the spectrometer ranged between 1000 Da to 100 kDa. The laser intensities ranged between 250 and 255.

The mass spectrometer data indicated that the SP was not degraded. HGFIN-SP interaction was studied by pre-treating the PS1 chips with 50% acetonitrile for 3 min. After this, the chips were incubated for 45 min with the following: 2.5 μg HGFIN (experimental sample), anti-Id2, an unrelated IgG regarding its ability to complex with SP and was therefore treated as a negative control, rabbit anti-SP (positive control) or 20 ng fibronectin, fragment III-C (positive control). The arrays were blocked for 25 min with 1M ethanolamine and washed with PBS+0.5% Triton X (2x) and a final PBS wash step. After this the chips were washed with PBS+Triton-x, PBS, rinsed with 5 mM Hepes and then dried. CHCA was applied and the non-covalently bound SP was detected with the SELDI-Time of Flight Mass spectrometer as described for the profiling studies for HGFIN.

C. Interactions Between HGFIN and SP

Since the HGFIN clone was retrieved through screening of cDNA libraries with an NK-1-specific probe the natural, high affinity ligand for NK-1 could interact with HGFIN. The coding region of HGFIN was cloned and the protein was prepared purified with a prokaryotic vector under the control of IPTG and the histidine tag of 19 aa. Western blots with anti-His (FIG. 4A) and proteomics studies (FIG. 4B) verified the purity of HGFIN consisting of the histidine tag at the predicted molecular mass of ~66 kDa.

Protein-protein interactions were performed with the PS-1 protein chip since this chip was determined to covalently bind HGFIN. SP was added to the chip and then detected with the SELDI system. The results showed a single peak at ~13000 Da (FIG. 4C, top chromatogram) indicating that the interaction between SP and HGFIN was non-covalent. Similar studies with HGFIN expressed in a eukaryotic vector in the absence of the HAT tag showed similar results, indicating that the tag protein was not responsible for the interaction between SP and HGFIN.

Fibronectin has been reported to bind SP. Therefore, this property of fibronectin was used as a positive control for SP interaction on the SELDI system. As expected, PS-I chips that were covalently coated with FN-IIIC and then incubated with SP showed a single peak at ~13000 Da (FIG. 4C, middle chromatogram). Similar results were shown with another positive control: rabbit anti-SP (covalently bound) and SP (FIG. 4C, lower chromatogram). No peak was detected in two negative controls, which consisted of bovine serum albumin or an unrelated antibody (anti-Id2) covalently bound to the surface of PS-1.

Computational studies were next used to devise a 3-D model to understand the interaction between HGFIN and SP. The 3-D structure of the PKD region from HGFIN (FIG. 3B) was generated based on the structure of the PKD region on the protein database (FIG. 3B). The structure of SP, shown in FIG. 3D was previously reported. The PKD region was selected since the putative spatial arrangement in the extra-cellular portion of HGFIN (FIG. 2) would allow contact with SP. Unlike a binding pocket in NK-1 for SP, there was no obvious pocket for PKD (FIG. 3A). However, the electrostatic differences between SP and PKD could allow us to model protein-protein interaction that might explain how the PKD regions of HGFIN might interact non-covalently with SP (FIG. 3C).

Example 4

A. Expression of HGFIN in Differentiated Immune/Hematopoietic Cells

Since the HGFIN cDNA was isolated from BM cell subsets, BM and PB mononuclear cells were screened using northern analyses to study the expression of HGFIN. BMNC represents proliferating progenitors and PBMC represents differentiated cells that could be derived from the BM progenitors. The results showed no detectable HGFIN mRNA in BMNC from five different healthy donors (FIG. 5A) while HGFIN expression was detectable in PBMC from the same donors (FIG. 5B). Since HGFIN was detected in cells that represent a predominant population of differentiated immune cells (PBMC), the results, shown in FIGS. 5A and 5B suggest that HGFIN could be associated with cell differentiation. To further investigate a role for HGFIN in cell differentiation, BMNC were stimulated with M-CSF or G-CSF. After the cells were >90% differentiated to monocytes and neutrophils, cells were analyzed for the expression of HGFIN mRNA by northern analyses. The results indicate that differentiation of BMNC to monocytes and neutrophils correlates with detectable HGFIN mRNA (FIG. 5A, Lanes 1 and 2).

To verify that the expression of HGFIN was not due to activation by the two cytokines, northern analyses were performed with BMNC cultured with M-CSF or G-CSF and then analyzed for HGFIN mRNA before the cells were differentiated. The results showed no detectable HGFIN mRNA (FIG. 5A, Lane 4), similar to unstimulated BMNC (FIG. 5A, Lane 3). Together the data indicated that HGFIN is preferentially expressed in differentiated immune and hematopoietic cells.

B. Relationship Between Id2 and HGFIN Expression in Differentiated BM Cells

As stated, Id2 is an inhibitor of cell differentiation (15). Thus Id2 would be expected to be detectable in BMNC cells and then down regulated after the cells differentiate. Since the HGFIN gene appears to be associated with cell differentiation (FIG. 5), studies were performed to determine its association with Id2. The reason for choosing this particular transcription factor among the Id family is because Id2 mediates terminal differentiation in progenitors with cell cycle arrest during granulopoiesis but its expression is down regulated after the cells differentiate (29,30). Furthermore, Id-2 expression is expressed in HL-60 cells, a granulocytic progenitor cell line (31).

Figure 6:
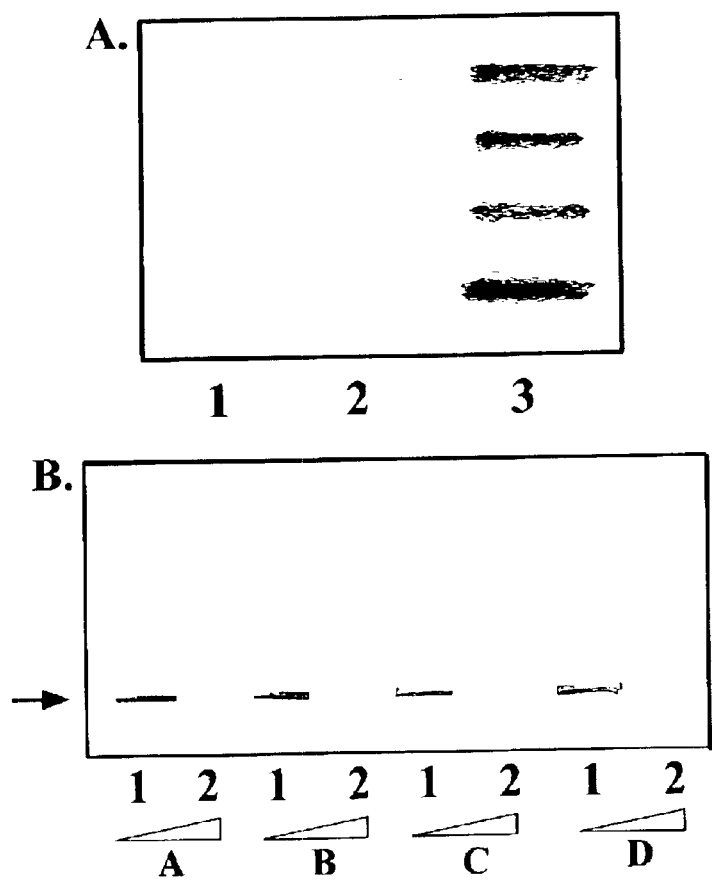
FIG. 6 shows the expression of Id2 in differentiated and undifferentiated BM cells. BMNC were differentiated with M-CSF or G-CSF. Total RNA or cell extracts were analyzed for Id2 mRNA or protein using northern analyses and western blots respectively. A. Northern analyses: Lane 1, G-CSF/granulocytes; Lane 2: M-CSF/monocytes; Lane 3: undifferentiated/media Arrows indicate a different BM donor. B. Western blots: Lanes 1, media/unstimulated; Lanes 2, G-CSF or M-CSF treated.

Northern blots were performed in four experiments, each with a different donor. The results showed that Id2 was undetectable in differentiated BMNC (FIG. 6A, Lane 1: M-CSF; Lane 2: G-CSF). However in undifferentiated BMNC (cultured in media alone), Id2 mRNA was detected in each of the four BM donors (FIG. 6A, Lane 3). In BMNC differentiated with M-CSF or G-CSF, the band for Id2 protein was very light to undetectable. The blot for cell extracts from M-CSF treated BMNC is shown in FIG. 6B, Lanes 2. The data presented in this section indicate that HGFIN is expressed in differentiated BM cells and that its expression correlates with down regulation of Id2, the transcription factor that inhibits cell differentiation.

Whole cell extracts from the same BM donor were studied for Id2 protein by western blots and the results showed a single band at 15 KDa in undifferentiated/BMNC (FIG. 6B, Lanes 1) and no detectable band in differentiated cells (FIG. 6B, Lanes 2). Lane 2 represents extracts from M-CSF or G-CSF-differentiated BMNC. The data presented in this section indicate that HGFIN is expressed in differentiated BM cells and that its expression correlates with down regulation of Id2, the transcription factor that inhibits cell differentiation.

C. Expression of HGFIN in Differentiated and Undifferentiated Myelomoncytic Cell Line HGFIN mRNA was studied in differentiated and undifferentiated HL-60 cells to determine if the expression of this gene was limited to normal BM progenitors. HL-60 cells were differentiated with chemical agents: TPA or DMSO for monocytes or granulocytes respectively. Similar to normal progenitors, HGFIN mRNA was detected in differentiated HL-60. HGFIN mRNA was undetectable in undifferentiated cells. The results show that HGFIN is expressed after differentiation of the myelomonocytic leukemic cell line, HL-60 to granulocytes and monocytes.

D. Expression of HGFIN in Activated Immune Cells

As differentiated immune cells express HGFIN (FIG. 5), studies were performed to determine if HGFIN was also expressed when these differentiated cells were activated. This question was addressed by stimulating PBMC with LPS for 8 and 16 h and then determined the levels of steady state HGFIN mRNA by northern analysis. Studies with PBMC from three different healthy donors A, B and C showed that LPS stimulation down regulated HGFIN expression at 16 h. There was no difference at 8 h. Consistent with HGFIN expression in PBMC (FIG. 5B), HGFIN mRNA was detected in the unstimulated PBMC. The data indicate that the expression of HGFIN in unstimulated, differentiated PBMC was down regulated following cell activation by a mitogen.

E. Expression of HGFIN in BM Stromal Cells

Figure 7A:
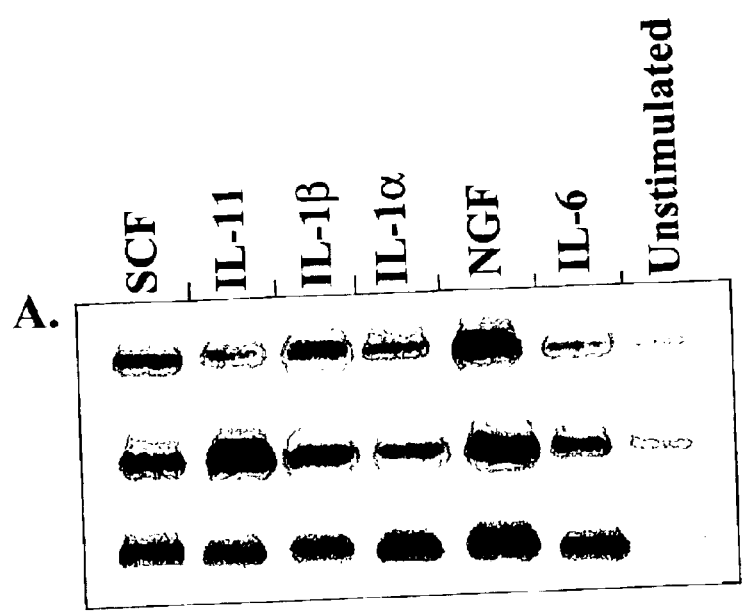
FIG. 7 shows the expression of HGFIN in BM stroma. Confluent stromal cells were stimulated with various hematopoietic relevant cytokines and then analyzed for HGFIN expression by northern analyses. The results are shown for three experiments, each with a different healthy donor (A). Band intensities were normalized with 18S rRNA and the induction over unstimulated cells are shown in B.
Figure 7B:
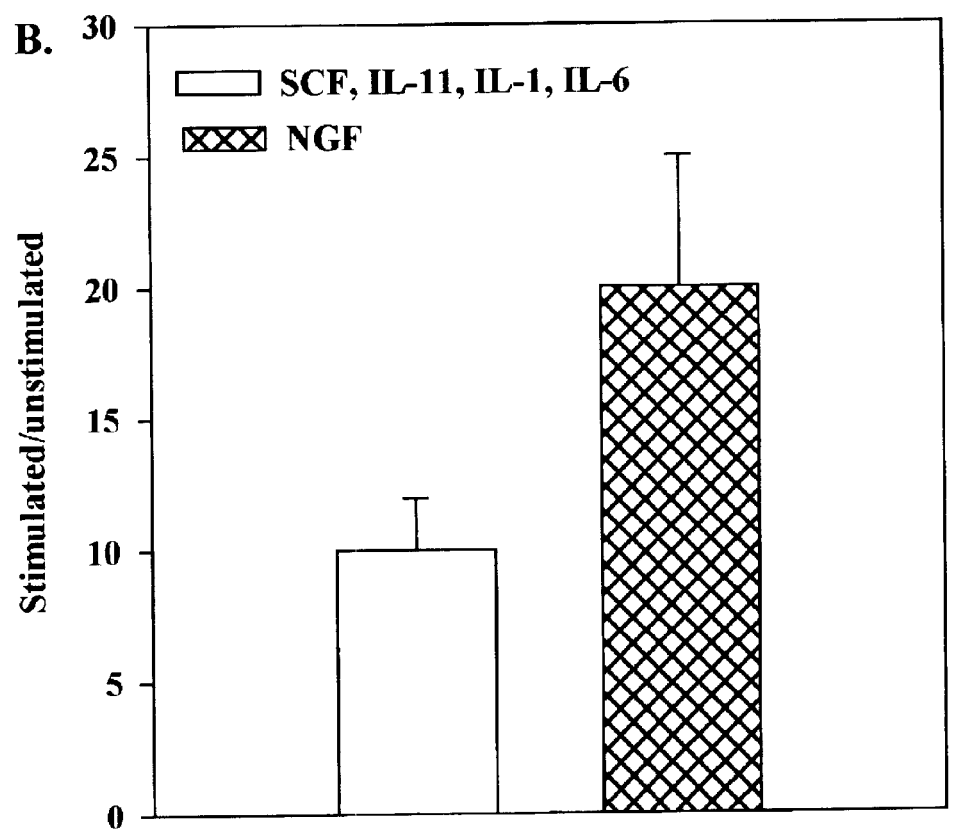

The mesenchymal/stromal cells of the BM produce most of the necessary soluble regulators that modulate BM organ functions (12). Since HGFIN expression was altered in activated PBMC, the next set of studies examined the role of HGFIN in activated BM stroma. The following stimulators were used: cytokines, SCF, IL-11, IL-1-($\alpha$, $\beta$ and IL-6 and a neurotrophic factor, NGF. The results of three studies, shown in FIG. 7A indicated that HGFIN was induced in each of the stimulated stromal cells. Densitometric scans were normalized with 18S rRNA and the fold (mean ±SD) increase-over unstimulated stroma is presented in FIG. 7B. The steady state levels of HGFIN mRNA in cultures stimulated with SCF, IL-11, IL-1$\alpha$/$\beta$ or IL-6 were comparable. However, together, the levels of HGFIN mRNA in the cytokine-stimulated cultures were much less than in stroma stimulated with NGF.

F. Expression of HGFIN in Different Tissues

To determine if HGFIN is expressed in tissues other than BM and immune cells, a northern blot was performed with a membrane from a commercial source, which has poly A from different tissues: Human MTN blot (Clontech, Palo Alto, Calif.). Except for mRNA isolated from the brain, the results showed a single band from the other tissues (FIG. 8A). The bands from the lung, liver, and skeletal muscle were less intense than the lanes from the other HGFIN expressing tissues. The reduced band intensities could not be due to differences in the mRNA loaded per lane since the MTN blots were equally intense for P-actin mRNA (not shown). The similarity in P-actin levels was consistent with the manufacturer's product information.

HGFIN is homologous to the nmb cDNA that was isolated in melanoma (27). The next set of studies screened cancer cell lines from human melanoma and breast cancer (T-47D and DU4475). Comparison was made with a normal mammary epithelial cell line (MCF-12A). Representative of three experiments, each performed with cell lines from a different passage is shown in FIG. 10B. Except for T-47D, each cell line tested showed single bands at the predicted size of 2.4 kb. A double band was shown for T4713, one at 2.4 kb and the other slightly bigger. The validity of the double band in the T-47D cell line was verified in three separate experiments using cell lines from different passages (data not shown). These results showed that HGFIN expression is not limited to BM and immune cells.

Example 5

Results of Analysis

Figure 8:
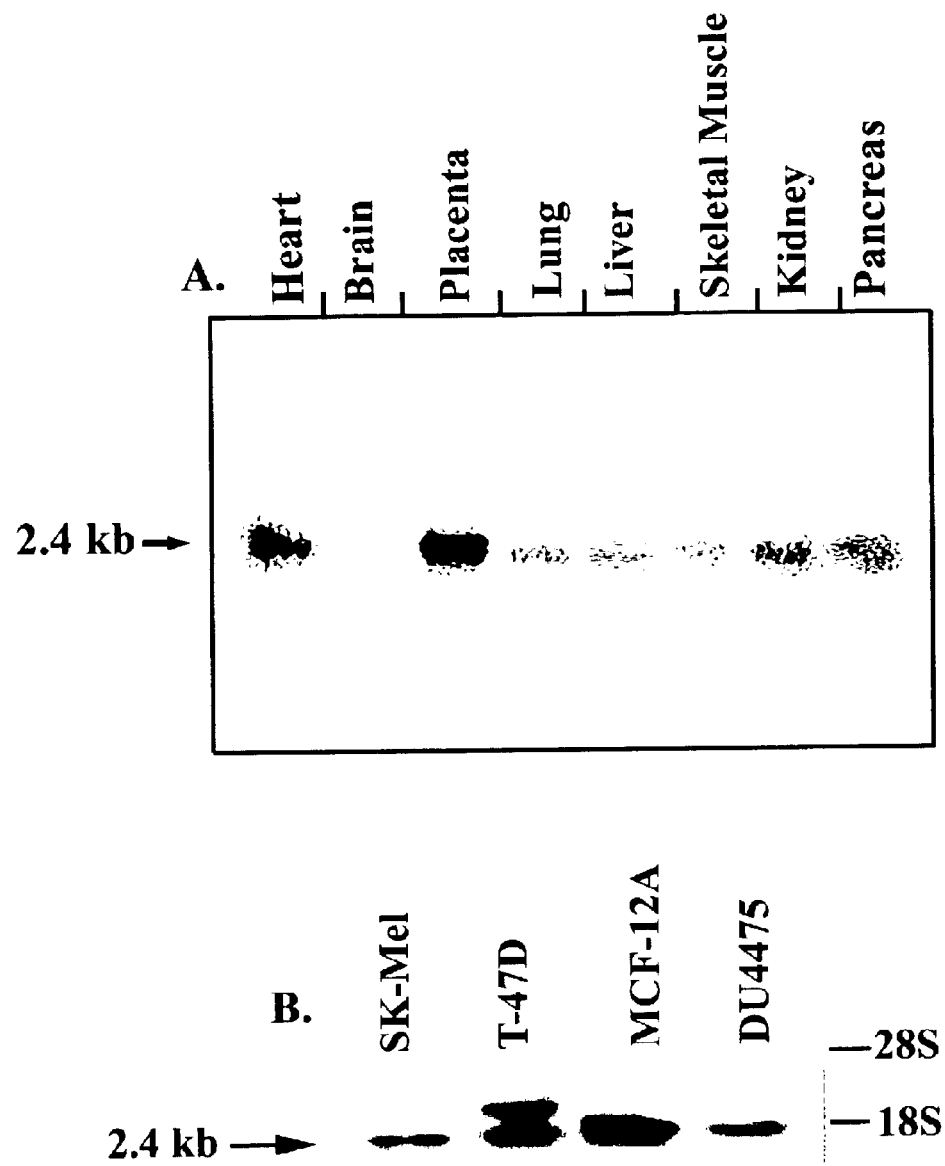
FIG. 8 shows the expression of HGFIN in different tissue. Membrane with mRNA from various tissues was hybridized with HGFIN cDNA probe (A). Total RNA was extracted from human melanoma, SK-Mel or breast cancer cell lines: T-47D and DU4475 or normal mammary epithelial cells, MCF-12A (B).

The present invention sets forth the association of the HGFIN gene with hematopoietic cell differentiation. Since the HGFIN gene is expressed in other tissues, it is possible that this gene could be involved in the differentiation of cells in other tissues (FIG. 8). The down regulation of HGFIN in immune cells stimulated with LPS was observed. LPS is a B-cell mitogen and despite terminal cell differentiation of B-cells, mitogens could mediate the polyclonal expansion of B-cells. The present inventors studied HGFIN expression in cells from a 'quiescent' differentiating state to the reversion into proliferating cells. Results suggest that differentiating cells may be prevented from proliferating in the event that HGFIN expression cannot be down regulated.

Also, over expression of HGFIN in proliferating cells such as BM progenitors may be polarized into terminal differentiation. This mechanism is applicable to leukemia and lymphoma, where the cells are at a checkpoint of proliferation. Further, the HGFIN gene could be involved in differentiation in other tissues where it is overexpressed as well. HL-60 was studied since it is a myelomonocytic leukemic cell line. These findings, as well as the data, which showed differences in HGFIN expression from studies with differentiated and predominantly proliferating BMNC are important in showing how HGFIN could be intervened in leukemia and perhaps lymphoma. As discussed above, specific antibodies to HGFIN (prepared in accordance with the methods described above) and studies on the spatial arrangement of HGFIN within a cell will further lead to a more comprehensive understanding of the biology of this gene and how it can better be used to treat blood related diseases.

The interaction between SP and the PKD region of HGFIN is important in the development of immune cells and erythrocytes in the BM since SP is a hematopoietic regulator (2). Proteomic analyses shows an interaction between SP and the PKD region of HGFIN (FIGS. 4 and 3C). This interaction may be important in regulating other functions, given SP's dual role as a proinflammatory peptide and as a hemapoietic regulator. For instance, SP may induce cytokines and other hematopoietic relevant factors in BM cell subsets and immune cells. Another relevance for this interaction is bone morphogenesis since SP is involved in bone metabolism (32). Furthermore, since SP binds to NK-1 (2, 7), which is the cDNA that was used to isolate the HGFIN clone during screening of the libraries, and since NK-1 is associated with several clinical disorders and is a target for drug development (33), molecules such as HGFIN with potential binding of SP could confound the treatments with drugs that target NK-1. Recent work by the present inventors, showed that SP can complex to fibronectin. The property of SP to bind proteins that share structural homology to its high affinity receptor, NK-1 could confound the biology of NK-1, which is associated with several clinical disorders and a target for drug development. During targeting of NK-1, the ligand, SP, could bind to other molecules such as HGFIN and fibronectin, part of the BM extracellular matrix proteins. In these cases, SP, which preferentially binds to NK-1 would be available to HGFIN at 'abnormal' levels and might mediate other functions through its interaction with HGFIN and other molecules. The model presented in FIG. 3C shows how such an interaction is possible since similar 3-D structure was observed for fibronectin, which shared a homologous region with NK-1 (17).

Figure 4:
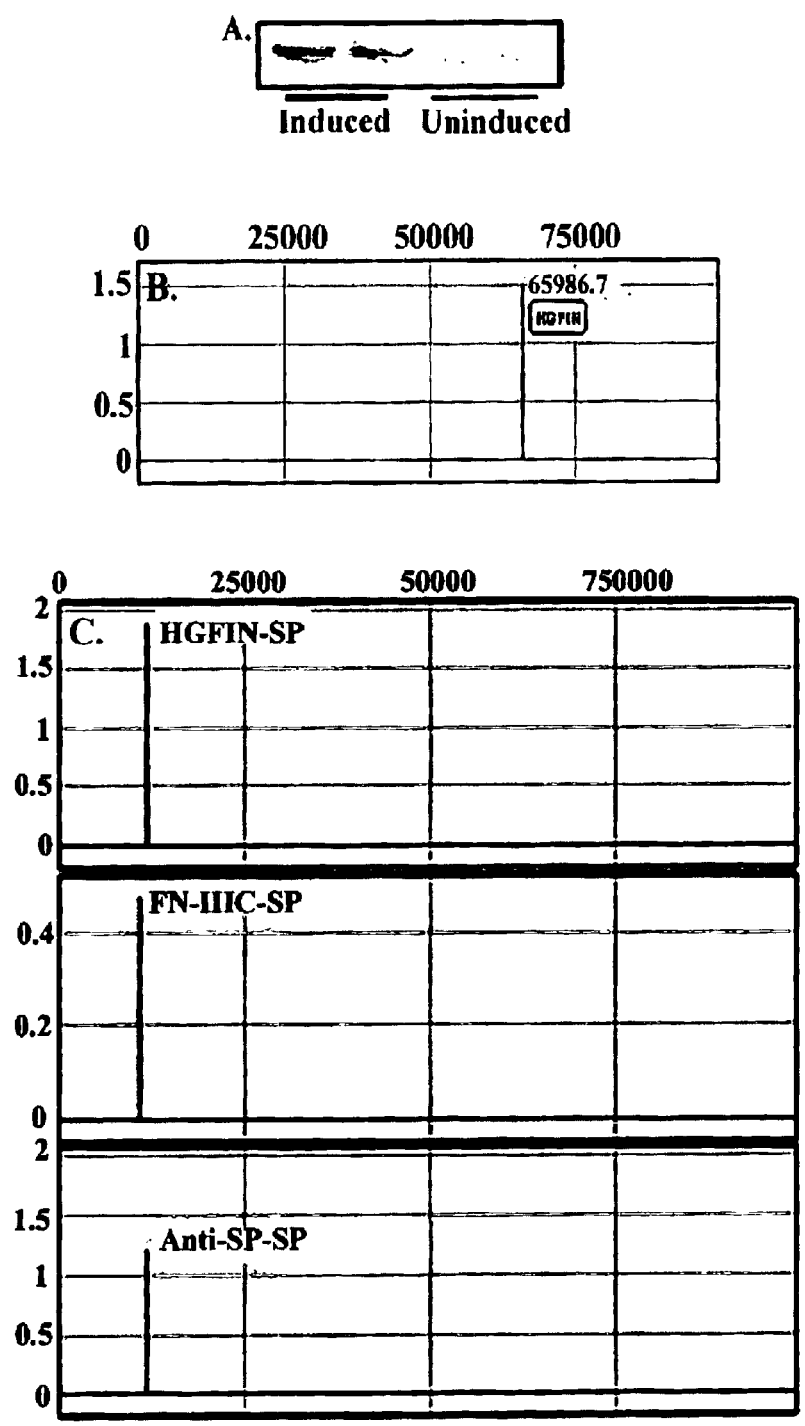
FIG. 4 shows mass spectra of SP. A. Western blots of proteins from IPTG-induced or uninduced pHAT10-HGFIN. Total protein from bacterial lysate (10 μg) was analyzed in western blots. Membranes were developed with rabbit anti-HAT as the primary antibody and Alk Phos conjugated goat anti-rabbit IgG as the secondary antibody. Alk Phos was developed with BCIP/NBT substrate. B. Mass spectrum of purified HGFIN-HAT with an NP-1 chip. C. PS-1 chips were covalently bound with HGFIN (top), FN-IIIC (middle) or rabbit anti-SP (bottom) and then incubated with 2 μg SP.

HGFIN induction in BM stromal cells of healthy subjects was different than in the differentiated hematopoietic cells (FIGS. 3 and 7). While HGFIN mRNA is undetectable in unstimulated stroma, it is induced by cytokines (FIG. 7). A compelling relevance for these findings is based on the importance of the BM stroma to regulate the proliferation and differentiation of hematopoietic stem and progenitor cells (12). In contrast to stromal cells, the expression of HGFIN in differentiated immune cells was blunted following cell stimulation. Together, these results indicate that HGFIN is important at two levels of the hematopoietic hierarchy: at the top where the stromal cells have major roles in regulating the hematopoietic stem cells (12) and at the terminal end where the cells are fully differentiated and are ready to exit the BM into the circulation and to the secondary lymphoid organs. The fact that HGFIN was down regulated when Id2 was upregulated and vice versa, indicates that the basic helix-loophelix family of transcription factors (34) may be important in the regulation of HGFIN.

As stated above, the foregoing is intended to be illustrative of the embodiments of the present invention, and are not intended to limit the invention in any way. Although the invention has been described with respect to the specific modifications described above, the details thereof are not to be construed as limitations, for it will be apparent that various equivalents, changes and modifications may be resorted to without departing from the spirit and scope thereof and it is understood that such equivalent embodiments are to be included herein.

References

1. Quinn, J. P., C. E. Fiskerstrand, L. Gerrard, A. MacKenzie, and C. M. Payne. 2000. Molecular models to analyse preprotachykinin-A expression and function. Neuropeptides 34:292–302.
2. Rameshwar, P. 1997. Substance P: A regulatory neuropeptide for hematopoiesis and immune functions. Clin. Immunol. Immunopath. 85:129–133.
3. Ho, W.-Z., J. P. Lai, X.-H. Zhu, M. Uvaydova, and S. D. Douglas. 1997. Human monocytes and macrophages express substance P and neurokinin-1 receptor. J Immunol. 159:5654–5660.
4. Maggi, C. A. 1996. Tachykinins in the autonomic nervous system. Pharmacol. Res. 33:161–170.
5. Tabarowski, Z., K. Gibson-Berry, and S. Y. Felten. 1996. Noradrenergic and peptidergic innervation of the mouse femur bone marrow. Acta. Histochem. 98:453–457.
6. Marriott, I., and K. L. Bost. 2000. IL-4 and IFN-γ up-regulate substance P receptor expression in murine peritoneal macrophages. J. Immunol. 165:182–191.
7. Krause, J. E., Y. Takeda, and A. D. Hershey. 1992. Structure, functions, and mechanisms of substance P receptor action. J. Invest. Dermatol. 98:2S-7S.
8. Rameshwar, P., A. Poddar, and P. Gascon. 1997. Hematopoietic regulation mediated by interactions among the neurokinins and cytokines. Leuk. Lymphoma 28:1–10.
9. Yao, R., P. Rameshwar, R. J. Donnelly, and A. Siegel. 1999. Neurokinin-1 expression and colocalization with glutamate and GABA in the hypothalamus of the cat. Mol. Brain Res. 71:149–158.
10. Abrahams, L. G., M. A. Rerutter, K. E. McCarson, and V. S. Seybold. 1999. Cyclic AMP regulates the expression of neurokinin 1 receptors by neonatal rat spinal neurons. J. Neurochem. 73:50–58.
11. Gerard, N. P., L. A. Garraway, R. L. Eddy, T. B. Shows, H. Iijima, J-L Paquet, and G. Gerard. 1991. Human substance P receptor (NK-1): organization of the gene, chromosome localization, and functional expression of cDNA clones. Biochemistry 30:10640–10646.
12. Muller-Sieburg, C. E., and E. Deryugina. 1995. The stromal cells'guide to the stem cell universe. Stem Cells 13:477–486.
13. Randall, T. D., and I. L. Weissman. 1998. Characterization of a population of cells in the bone marrow that phenotypically mimics hematopoietic stem cells: resting stem cells or mystery population. Stem Cells 16:38–48.
14. Roodman, G. D. Cell biology of the osteoclast. 1999. Exp. Hematol. 27:1229–1241.
15. Biggs, J., E. V. Murphy, and M. A. Israel. 1992. A human Id-like helix-loop-helix protein expression during early development. Proc. Nat'l Acad. Sci. USA 89:1512–1516.
16. Singh, D., D. D. Joshi, M. Hameed, J. Qian, P. Gascón, P. B. Maloof, A. Mosenthal, and P. Rameshwar. 2000. Increased expression of preprotachykinin-1 and neurokinin receptors in human breast cancer cells. Implications for bone marrow metastasis. Proc. Nat'l Acad. Sci. USA 97:388–393.
17. Rameshwar, P., D. D. Joshi, P. Yadav, P. Gascón, J. Qian, V. T. Chang, A. Anjaria, J. S. Harrison, and S. Xiaosong. 2001. Mimicry between neurokinin-1 and fibronectin may explain the transport and stability of increased substance P-immunoreactivity in patients with bone marrow fibrosis. Blood 97:3025–3031.
18. Miura, Y., Y. Tohyama, T. Hishita, A. Lala, E. De Nardin, Y. Yoshida, H. Yamamura, T. Uchiyama, and K. Tohyama. 2000. Pyk2 and Syk participate in functional activation of granulocytic HL-60 cells in a different manner. Blood 96:1733–1739.
19. Hegde, S. P., J. Zhao, R. A. Ashmum, and L. H. Shapiro. 1999. c-Maf induces monocytic differentiation and apoptosis in bipotent myeloid progenitors. Blood 94:1578–1589.
20. Rameshwar, P., A. Poddar, G. Zhu, and P. Gascón. 1997. Receptor induction regulates the synergistic effects of substance P with IL-1 and PDGF on the proliferation of bone marrow fibroblasts. J. Immunol. 158:3417–3424.
21. Corpet, F., J. Gouzy, and D. Kahn. 1998. The ProDom database of protein domain families. Nucleic Acid Res. 26:323–326.
22. Bairoch, A., P. Bucher, and K. Hofmann. 1997. The PROSITE database, its status in 1997. Nucleic Acid Res. 25:217–221.
23. Rost, B., and C. Sander. 1993. Prediction of protein structure at better than 70% accuracy. J. Mol. Biol. 232:584–599.
24. Rost, B., and C. Sander. 1994. Combining evolutionary information and neural networks to predict protein secondary structure. Proteins 19:55–72.
25. Sonnhammer, E. L., G. Heijue, and A. Krogh. 1998. A hidden Markov model for predicting transmembrane helices in protein sequences. p.175–182. In Ed J. Glasgow, T. Littlejohn, F. Major, R. Lathrop, D. Sankoff, and C. Sensen (ed.), Proceedings of 6th International Conference on Intelligent Systems for Molecular Biology. Menlo Park, Calif.
26. Rameshwar, P., R. Narayanan, J. Qian, T. N. Denny, C. Colon, and P. Gascón. 2000. NF-KB as a central mediator in the induction of TGF-P in monocytes from patients with idiopathic myelofibrosis: An inflammatory response beyond the realm of homeostasis. J. Immunol. 165:2271–2277.
27. Weterman, M. A. J., N. Ajubi, 1. M. R. van Dinter, W. G. J. Degen, G. N. P. van Muijen. 1995. nmb, a novel gene, is expressed in low-metastatic human melanoma cell lines and xenografts. Int. J. Cancer 60:73–81.
28. The International Poleystic Kidney Disease Consortium. 1995. Polycystic kidney disease: The complete structure of the PKD 1 gene and its protein. Cell 81:289–298.
29. Cooper, C. L., and P. E. Newburger. 1998. Differential expression of Id genes in multipotent myeloid progenitor cells: Id-1 is included by early and late-acting cytokines while Id-2 is selectively induced by cytokines that drive terminal granulocytic differentiation. J. Cell. Biochem. 71:277–285.
30. Ishiguro, A., K. S. Spirin, M. Shiohara, A. Tobler, A. F. Gombart, M. A. Israel, J. D. Norton, and H. P. Koffler. 1996. Id2 expression increases with differentiation of human myeloid cells. Blood 87:5225–5231.
31. Norton, J. D., R. W. Deed, G. Craggs, and F. Sablitzky. 1998. Id helix-loop-helix proteins in cell growth and differentiation. Trends Cell Biol. 8:58–65.
32. Adamus, M. A., and Z. J. Dabrowski. 2001. Effect of the neuropeptide substance P on the rat bone marrow-derived osteogenic cells in vitro. J. Cell. Biochem. 81:499–506.
33. Rupniak, N. M. 2000. Preclinical pharmacology of tachykinin receptor anagonists. Tachykinins 2000. 2a.
34. Massari, M. E., and C. Murre. 2000. Helix-Loop-Helix proteins: Regulators of transcription in eucaryotic organisms. Mol. Cell. Biol. 20:429–440.

What is claimed is:

1. An isolated polynucleotide, comprising a Hematopoietic Growth Factor Inducible Neurokinin-I type nucleotide sequence that has at least 97% identity to SEQ ID NO:1, said identity being calculated over the entire length of SEQ ID NO:1.

2. The polynucleotide of claim 1, comprising the nucleotide sequence of SEQ ID NO:1.

3. A vector comprising a polynucleotide of claim 1, wherein said polynucleotide encodes a Hematopoietic Growth Factor Inducible Neurokinin-I type polypeptide.

4. The vector of claim 3, wherein the Hematopoietic Growth Factor Inducible Neurokinin-I type polypeptide further comprises the amino acid sequence of SEQ ID NO:2.

5. An isolated host cell comprising the vector of claim 3.

6. A process for producing an Hematopojetic Growth Factor Inducible Neurokinin-I type polypeptide comprising culturing a host of claim 5 under conditions sufficient for the production of said polypeptide and recovering the polypeptide from the culture.

7. A process for producing a cell which produces a Hematopoietic Growth Factor Inducible Neurokinin-I type polypeptide comprising transforming, transducing or transfecting an isolated host cell with the vector of claim 3 such that the host cell, under appropriate culture conditions, produces an HGFIN polypeptide.

8. The process of claim 7, wherein the cell is a bone marrow derived cell removed from the body of a subject.

* * * * *

SEQUENCE LISTING

<160> NUMBER OF SEQ ID NOS: 4

<210> SEQ ID NO 1
<211> LENGTH: 2661
<212> TYPE: DNA
<213> ORGANISM: Homo sapiens

<400> SEQUENCE: 1
cggcacgagg gcccagagga ataagttaac cttggtgcct gcgtccgtga gaattcagca      60
tggaatgtct ctactatttc ctgggatttc tgctcctggc tgcaagattg ccacttgatg     120

-continued

```
ccgccaaacg atttcatgat gtgctgggca atgaaagacc ttctgcttac atgagggagc      180
acaatcaatt aaatggctgg tcttctgatg aaaatgactg gaatgaaaaa ctctacccag      240
tgtggaagcg gggagacatg aggtggaaaa actcctggaa gggaggccgt gtgcaggcgg      300
tcctgaccag tgactcacca gccctcgtgg gctcaaatat aacatttgcg gtgaacctga      360
tattccctag atgccaaaag gaagatgcca atggcaacat agtctatgag aagaactgca      420
gaaatgaggc tggtttatct gctgatccat atgtttacaa ctggacagca tggtcagagg      480
acagtgacgg ggaaaatggc accggccaaa gccatcataa cgtcttccct gatgggaaac      540
cttttcctca ccaccccgga tggagaagat ggaatttcat ctacgtcttc cacacacttg      600
gtcagtattt ccagaaattg ggacgatgtt cagtgagagt ttctgtgaac acagccaatg      660
tgacacttgg gcctcaactc atggaagtga ctgtctacag aagacatgga cgggcatatg      720
ttcccatcgc acaagtgaaa gatgtgtacg tggtaacaga tcagattcct gtgtttgtga      780
ctatgttcca gaagaacgat cgaaattcat ccgacgaaac cttcccaaag atctccccat      840
tatgtttgat gtcctgattc atgatcctag ccacttcctc aattattcta ccattaacta      900
caagtggagc ttcggggata atactggcct gtttgtttcc accaatcata ctgtgaatca      960
cacgtatgtg ctcaatggaa ccttcagcct taacctcact gtgaaagctg cagcaccagg     1020
accttgtccg ccaccgccac caccacccag accttcaaaa cccaccccctt ctttaggacc     1080 tgctggtgac aaccccctgg agctgagtag gattcctgat gaaaactgcc agattaacag     1140
atatggccac tttcaagcca ccatcacaat tgtagaggga atcttagagg ttaacatcat     1200
ccagatgaca gacgtcctga tgccggtgcc atggcctgaa agctccctaa tagactttgt     1260
cgtgacctgc caagggagca ttcccacgga ggtctgtacc atcatttctg accccacctg     1320
cgagatcacc cagaacacag tctgcagccc tgtggatgtg gatgagatgt gtctgctgac     1380
tgtgagacga accttcaatg ggtctgggac gtactgtgtg aacctcaccc tgggggatga     1440
cacaagcctg gctctcacga gcaccctgat ttctgttcct gacagagacc cagcctcgcc     1500
tttaaggatg gcaaacagtg ccctgatctc cgttggctgc ttggccatat ttgtcactgt     1560
gatctccctc ttggtgtaca aaaaacacaa ggaatacaac ccaatagaaa atagtcctgg     1620
gaatgtggtc agaagcaaag gcctgagtgt ctttctcaac cgtgcaaaag ccgtgttctt     1680
cccgggaaac caggaaaagg atccgctact caaaaaccaa gaatttaaag gagtttctta     1740
aatttcgacc ttgtttctga agctcacttt tcagtgccat tgatgtgaga tgtgctggag     1800
tggctattaa cctttttttc ctaaagatta ttgttaaata gatattgtgg tttggggaag     1860
ttgaattttt tataggttaa atgtcatttt agagatgggg agaggggatta tactgcaggc     1920 agcttcagcc atgttgtgaa actgataaaa gcaacttagc aaggcttctt ttcattattt     1980
tttatgtttc acttataaag tcttaggtaa ctagtaggat agaaacactg tgtcccgaga     2040
gtaaggagag aagctactat tgattagagc ctaacccagg ttaactgcaa gaagaggcgg     2100
gatactttca gctttccatg taactgtatg cataaagcca atgtagtcca gtttctaaga     2160
tcatgttcca agctaactga atcccacttc aatacacact catgaactcc tgatggaaca     2220
ataacaggcc caagcctgtg gtatgatgtg cacacttgct agactcagaa aaaatactac     2280
tctcataaat gggtgggagt attttggtga caacctactt tgcttggctg agtgaaggaa     2340
tgatattcat atattcattt attccatgga catttagtta gtgctttta tataccaggc     2400 atgatgctga gtgacactct tgtgtatatt tccaaatttt tgtatagtcg ctgcacatat     2460
```

```
ttgaaatcaa aatattaaga ctttccaaaa atttggtccc tggttttca tggcaacttg    2520 atcagtaagg atttcccctc tgtttggaac taaaaccatt tactatatgt tagacaagac    2580 atttttttt tttccttcct gaaaaaaaa tgagggaaga gacaaaaaaa aaaaaaaaa      2640 aaaaaaaaaa aaaaaaaaa a                                                2661
```

<210> SEQ ID NO 2
<211> LENGTH: 560
<212> TYPE: PRT
<213> ORGANISM: Homo sapiens

<400> SEQUENCE: 2

```
Met Glu Cys Leu Tyr Tyr Phe Leu Gly Phe Leu Leu Ala Ala Arg
1               5                   10                  15

Leu Pro Leu Asp Ala Ala Lys Arg Phe His Asp Val Leu Gly Asn Glu
                20                  25                  30

Arg Pro Ser Ala Tyr Met Arg Glu His Asn Gln Leu Asn Gly Trp Ser
            35                  40                  45

Ser Asp Glu Asn Asp Trp Asn Glu Lys Leu Tyr Pro Val Trp Lys Arg
50                  55                  60

Gly Asp Met Arg Trp Lys Asn Ser Trp Lys Gly Gly Arg Val Gln Ala
65                  70                  75                  80

Val Leu Thr Ser Asp Ser Pro Ala Leu Val Gly Ser Asn Ile Thr Phe
                85                  90                  95

Ala Val Asn Leu Ile Phe Pro Arg Cys Gln Lys Glu Asp Ala Asn Gly
            100                 105                 110

Asn Ile Val Tyr Glu Lys Asn Cys Arg Asn Glu Ala Gly Leu Ser Ala
        115                 120                 125

Asp Pro Tyr Val Tyr Asn Trp Thr Ala Trp Ser Glu Asp Ser Asp Gly
130                 135                 140

Glu Asn Gly Thr Gly Gln Ser His His Asn Val Phe Pro Asp Gly Lys
145                 150                 155                 160

Pro Phe Pro His His Pro Gly Trp Arg Arg Trp Asn Phe Ile Tyr Val
                165                 170                 175

Phe His Thr Leu Gly Gln Tyr Phe Gln Lys Leu Gly Arg Cys Ser Val
            180                 185                 190

Arg Val Ser Val Asn Thr Ala Asn Val Thr Leu Gly Pro Gln Leu Met
        195                 200                 205

Glu Val Thr Val Tyr Arg Arg His Gly Arg Ala Tyr Val Pro Ile Ala
210                 215                 220

Gln Val Lys Asp Val Tyr Val Val Thr Asp Gln Ile Pro Val Phe Val
225                 230                 235                 240

Thr Met Phe Gln Lys Asn Asp Arg Asn Ser Ser Asp Glu Thr Phe Leu
                245                 250                 255

Lys Asp Leu Pro Ile Met Phe Asp Val Leu Ile His Asp Pro Ser His
            260                 265                 270

Phe Leu Asn Tyr Ser Thr Ile Asn Tyr Lys Trp Ser Phe Gly Asp Asn
        275                 280                 285

Thr Gly Leu Phe Val Ser Thr Asn His Thr Val Asn His Thr Tyr Val
290                 295                 300

Leu Asn Gly Thr Phe Ser Leu Asn Leu Thr Val Lys Ala Ala Ala Pro
305                 310                 315                 320

Gly Pro Cys Pro Pro Pro Pro Pro Pro Arg Pro Ser Lys Pro Thr
                325                 330                 335
```

-continued

```
Pro Ser Leu Gly Pro Ala Gly Asp Asn Pro Leu Glu Leu Ser Arg Ile
            340                 345                 350
Pro Asp Glu Asn Cys Gln Ile Asn Arg Tyr Gly His Phe Gln Ala Thr
            355                 360                 365
Ile Thr Ile Val Glu Gly Ile Leu Glu Val Asn Ile Ile Gln Met Thr
            370                 375                 380
Asp Val Leu Met Pro Val Pro Trp Pro Glu Ser Ser Leu Ile Asp Phe
385                 390                 395                 400
Val Val Thr Cys Gln Gly Ser Ile Pro Thr Glu Val Cys Thr Ile Ile
                405                 410                 415
Ser Asp Pro Thr Cys Glu Ile Thr Gln Asn Thr Val Cys Ser Pro Val
            420                 425                 430
Asp Val Asp Glu Met Cys Leu Leu Thr Val Arg Arg Thr Phe Asn Gly
            435                 440                 445
Ser Gly Thr Tyr Cys Val Asn Leu Thr Leu Gly Asp Asp Thr Ser Leu
            450                 455                 460
Ala Leu Thr Ser Thr Leu Ile Ser Val Pro Asp Arg Asp Pro Ala Ser
465                 470                 475                 480
Pro Leu Arg Met Ala Asn Ser Ala Leu Ile Ser Val Gly Cys Leu Ala
                485                 490                 495
Ile Phe Val Thr Val Ile Ser Leu Leu Val Tyr Lys Lys His Lys Glu
                500                 505                 510
Tyr Asn Pro Ile Glu Asn Ser Pro Gly Asn Val Val Arg Ser Lys Gly
            515                 520                 525
Leu Ser Val Phe Leu Asn Arg Ala Lys Ala Val Phe Phe Pro Gly Asn
        530                 535                 540
Gln Glu Lys Asp Pro Leu Leu Lys Asn Gln Glu Phe Lys Gly Val Ser
545                 550                 555                 560

<210> SEQ ID NO 3
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 3
cggggtacca tggaatgtct ctacta                                          26

<210> SEQ ID NO 4
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 4
ccggaattct cgaaatttaa gaaact                                          26
```